(12) United States Patent
Inoue et al.

(10) Patent No.: US 7,771,844 B2
(45) Date of Patent: *Aug. 10, 2010

(54) ORGANIC METAL COMPLEX AND PHOTOELECTRONIC DEVICE, LIGHT-EMITTING ELEMENT AND LIGHT-EMITTING DEVICE USING THE SAME

(75) Inventors: Hideko Inoue, Atsugi (JP); Satoko Shitagaki, Atsugi (JP); Satoshi Seo, Kawasaki (JP)

(73) Assignee: Semiconductor Energy Laboratory Co., Ltd, Atsugi-shi, Kanagawa-ken (JP)

( * ) Notice: Subject to any disclaimer, the term of this patent is extended or adjusted under 35 U.S.C. 154(b) by 715 days.

This patent is subject to a terminal disclaimer.

(21) Appl. No.: 11/274,327

(22) Filed: Nov. 16, 2005

(65) Prior Publication Data

US 2006/0159955 A1 Jul. 20, 2006

(30) Foreign Application Priority Data

Dec. 3, 2004 (JP) ............................ 2004-352077

(51) Int. Cl.
*H01L 51/54* (2006.01)
*C09K 11/06* (2006.01)

(52) U.S. Cl. ....................... 428/690; 428/917; 313/504; 257/E51.044; 544/225

(58) Field of Classification Search ........................ None
See application file for complete search history.

(56) References Cited

U.S. PATENT DOCUMENTS

| | | | |
|---|---|---|---|
| 6,303,238 B1 | 10/2001 | Thompson et al. | |
| 6,821,645 B2 | 11/2004 | Igarashi et al. | |
| 6,821,646 B2 | 11/2004 | Tsuboyama et al. | |
| 6,835,469 B2 | 12/2004 | Kwong et al. | |
| 6,911,271 B1 | 6/2005 | Lamansky et al. | |
| 6,939,624 B2 | 9/2005 | Lamansky et al. | |
| 6,953,628 B2 | 10/2005 | Kamatani et al. | |
| 7,094,477 B2 | 8/2006 | Kamatani et al. | |
| 7,147,935 B2 | 12/2006 | Kamatani et al. | |
| 7,220,495 B2 | 5/2007 | Tsuboyama et al. | |
| 7,238,437 B2 | 7/2007 | Igarashi et al. | |
| 7,238,806 B2 * | 7/2007 | Inoue et al. | 544/225 |
| 7,339,317 B2 | 3/2008 | Yamazaki | |
| 7,381,479 B2 | 6/2008 | Lamansky et al. | |
| 7,400,087 B2 | 7/2008 | Yamazaki | |
| 7,413,816 B2 | 8/2008 | Inoue et al. | |
| 2001/0019782 A1 | 9/2001 | Igarashi et al. | |
| 2001/0045565 A1 | 11/2001 | Yamazaki | |
| 2003/0059646 A1* | 3/2003 | Kamatani et al. | 428/690 |
| 2003/0068526 A1 | 4/2003 | Kamatani et al. | |
| 2005/0003233 A1 | 1/2005 | Igarashi et al. | |
| 2005/0191527 A1* | 9/2005 | Fujii et al. | 428/917 |
| 2005/0208335 A1 | 9/2005 | Kamatani et al. | |
| 2005/0233170 A1 | 10/2005 | Yamazaki | |
| 2005/0242715 A1 | 11/2005 | Inoue et al. | |
| 2007/0213527 A1 | 9/2007 | Inoue et al. | |
| 2007/0241667 A1* | 10/2007 | Ohsawa et al. | 313/504 |
| 2008/0076922 A1 | 3/2008 | Inoue et al. | |
| 2008/0113216 A1 | 5/2008 | Inoue et al. | |
| 2008/0281098 A1 | 11/2008 | Lamansky et al. | |

FOREIGN PATENT DOCUMENTS

| | | |
|---|---|---|
| EP | 1 191 612 | 3/2002 |
| EP | 1 348 711 | 10/2003 |
| EP | 1 349 435 | 10/2003 |
| EP | 1 574 514 | 9/2005 |
| EP | 1 690 866 | 8/2006 |
| JP | 63-159856 | 7/1988 |
| JP | 06-207169 | 7/1994 |
| JP | 2001-247859 | 9/2001 |
| JP | 2003-040873 | 2/2003 |
| JP | 2003-058473 | 2/2003 |
| JP | 2004-155728 | 6/2004 |
| JP | 2005-239648 | 9/2005 |

(Continued)

OTHER PUBLICATIONS

Fujii et al., "Highly Efficient and Vivid-Red Phosphors Bearing 2,3-Diphenylquinoxaline Units and Their Application to Organic Light-Emitting Devices," IEICE Trans. Electron, vol. E-87-C, No. 12, Dec. 1, 2004, pp. 2119-2121.

(Continued)

*Primary Examiner*—Marie R. Yamnitzky
(74) *Attorney, Agent, or Firm*—Eric J. Robinson; Robinson Intellectual Property Law Office, P.C.

(57) ABSTRACT

It is an object of the present invention to provide a substance that can emit phosphorescence. Further, it is an object of the present invention to provide a light emitting element with favorable color purity. The present invention provides an organometallic complex having a structure represented by a general formula (1). A light emitting element that can exhibit red or reddish emission of light with favorable color purity can be obtained by using the organometallic complex of the present invention as aluminescent substance. In addition, a light emitting element that can emit light efficiently can be obtained by using the organometallic complex of the present invention as a sensitizer.

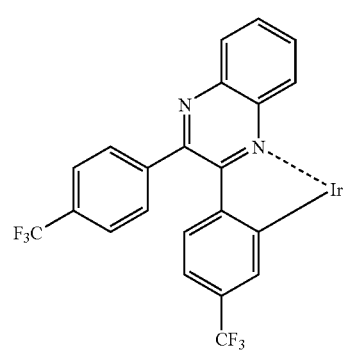

(1)

49 Claims, 12 Drawing Sheets

FOREIGN PATENT DOCUMENTS

| | | |
|---|---|---|
| JP | 2006-073992 | 3/2006 |
| JP | 2006-182775 | 7/2006 |
| JP | 3810789 | 8/2006 |
| WO | WO 00/70655 | 11/2000 |
| WO | WO 01/41512 | 6/2001 |
| WO | WO 02/15645 | 2/2002 |
| WO | WO 02/045466 | 6/2002 |
| WO | WO 03/033617 | 4/2003 |
| WO | WO 2005/054261 | 6/2005 |
| WO | WO 2005/115061 | 12/2005 |

OTHER PUBLICATIONS

C.W. Tang et al., "Organic Electroluminescent Diodes," Applied Physics Letters, vol. 51, No. 12, Sep. 21, 1987, pp. 913-915.

T. Tsutsui, "Mechanism of Organic EL Element and Luminous Efficiency," Textbook of the 3$^{rd}$ Seminar at Division of Organic Molecular Electronics and Bioelectronics, The Japanese Society of Applied Physics, Jan. 1, 1993, pp. 31-37.

Tsutsui et al., "High Quantum Efficiency in Organic Light-Emitting Devices with Iridium-Complex as a Triplet Emissive Center," Japanese Journal of Applied Physics, vol. 38, 1999, pp. L1502-L1504.

Nishi et al., "High Efficiency TFT-OLED Display with Iridium-Complex as Triplet Emissive Center," Proceedings of the 10$^{th}$ International Workshop on Inorganic and Organic Electroluminescence (EL'00), Dec. 4-7, 2000, pp. 353-356.

Tsutsui et al., "Electroluminescence in Organic Thin Films," Photochemical Processes in Organized Molecular Systems, 1991, pp. 437-450.

Baldo et al., "Highly Efficient Phosphorescent Emission from Organic Electroluminescent Devices," Letters to Nature, vol. 395, Sep. 10, 1998, pp. 151-154.

Baldo et al., "Very High-Efficiency Green Organic Light-Emitting Devices Based on Electrophosphorescence," Applied Physics Letters, vol. 75, Jul. 5, 1999, pp. 4-6.

Thompson et al., "Phosphorescent Materials and Devices," Proceedings of the 10$^{th}$ International Workshop on Inorganic and Organic Electroluminescence (EL'00), Dec. 4-7, 2000, pp. 35-38.

Fujii et al., "Efficient Red Organometallic Phosphors Bearing 2,3-Diphenylquinoxalines and Their Application to Electrophosphorescent Diodes," Proceedings of Organic Materials for Electronics and Photonics 2004, (one page; no page number).

International Search Report (Application No. PCT/JP2004/018079) dated Apr. 5, 2005.

Written Opinion (Application No. PCT/JP2004/018079) dated Apr. 5, 2005.

O'Brien et al., Improved energy transfer in electrophosphorescent devices, Appl. Phys. Lett. (Applied Physics Letters), vol. 74, No. 3, Jan. 18, 1999, pp. 442-444.

Baldo et al., High-efficiency fluorescent organic light-emitting devices using a phosphorescent sensitizer, Nature, vol. 403, Feb. 17, 2000, pp. 750-753.

Duan et al., New Iridium Complexes as Highly Efficient Orange-Red Emitters in Organic Light-Emitting Diodes, Adv. Mater. (Advanced Materials), vol. 15, No. 3, Feb. 5, 2003, pp. 224-228.

Kulikova et al., Effects of the Nature of the Ligand Environment and Metal Center on the Optical and Electrochemical Properties of Platinum(II) and Palladium(II) Ethylenediamine Complexes with Heterocyclic Cyclometalated Ligands, Russian Journal of General Chemistry, vol. 70, No. 2, Feb. 1, 2000, pp. 163-170.

Steel et al., Cyclometallated compounds. Part V. Double cyclopalladation of diphenyl pyrazines and related ligands, Journal of Organometallic Chemistry, vol. 395, No. 3, 1990, pp. 359-373.

Balashev et al., Synthesis and Properties of Palladium(II) and Platinum(II)(2,3-diphenylquinoxalinato-C,N)ethylenediamine Complexes, Russian Journal of General Chemistry, vol. 69, No. 8, Aug. 1, 1999, pp. 1348-1349.

Rasmussen et al., Synthesis and Characterization of a Series of Novel Rhodium and Iridium Complexes Containing Polypyridyl Bridging Ligands: Potential Uses in the Development of Multimetal Catalysts for Carbon Dioxide Reduction, Inorg. Chem. (Inorganic Chemistry), vol. 29, No. 20, 1990, pp. 3926-3932.

Zhang et al., Synthesis and Photoluminescence of a New Red Phosphorescent Iridium(III) Quinoxaline Complex, Chinese Chemical Letters, vol. 15, No. 11, 2004, pp. 1349-1352.

Seo et al., P-132: Long-Lived Deeply Red Phosphorescent OLEDs Based on Electrochemically Stable Ir Complexes, SID Digest '05: SID International Symposium Digest of.Technical Papers, vol. 36, 2005, pp. 806-809.

Lewis, Hawley's Condensed Chemical Dictionary, Twelfth Edition, p. 594, (1993).

Jakubke et al., Concise Encyclopedia Chemistry, p. 490, (1993).

Parker, McGraw-Hill Dictionary of Chemical Terms, Third Edition, p. 200, (1984).

Ito et al., Asymmetric Synthesis of Helical Poly(quinoxaline-2,3-diyl)s by Palladium-Mediated Polymerization of 1,2-Diisocyanobenzenes: Effective Control of the Screw-Sense by a Binaphthyl Group at the Chain-End, J. Am. Chem. Soc. (Journal of the American Chemical Society), vol. 120, 1998, pp. 11880-11893.

Ito et al., Living Polymerization of 1,2-Diisocyanoarenes Promoted by (Quinoxalinyl)nickel Complexes, Polymer Journal, vol. 24, No. 3, Jan. 1, 1992, pp. 297-299.

Yamamoto et al., Preparation of New-Electron-Accepting π-Conjugated Polyquinoxalines. Chemical and Electrochemical Reduction, Electrically Conducting Properties, and Use in Light-Emitting Diodes, J. Am. Chem. Soc. (Journal of the American Chemical Society), vol. 118, No. 16, Jan. 1, 1996, pp. 3930-3937.

International Search Report (Application No. PCT/JP2005/009310) dated Aug. 30, 2005.

Written Opinion (Application No. PCT/JP2005/009310) dated Aug. 30, 2005.

International Search Report (Application No. PCT/JP2005/022593) dated Mar. 14, 2006.

Written Opinion (Application No. PCT/JP2005/022593) dated Mar. 14, 2006.

International Search Report (Application No. PCT/JP2005/022507) dated Feb. 21, 2006.

Written Opinion (Application No. PCT/JP2005/022507) dated Feb. 21, 2006.

Patani et al., Bioisosterism: A Rational Approach in Drug Design, Chemical Review, vol. 96, No. 8, 1996, pp. 3147-3176.

Search Report (Application No. 04799935.4) dated Jan. 23, 2009.

Brooks et al., "Synthesis and Characterization of Phosphorescent Cyclometalated Platinum Complexes," Inorganic Chemistry, vol. 41, No. 12, pp. 3055-3066, 2002, (published on Web May 10, 2002).

* cited by examiner

ORGANIC METAL COMPLEX AND PHOTOELECTRONIC DEVICE, LIGHT-EMITTING ELEMENT AND LIGHT-EMITTING DEVICE USING THE SAME

FIELD OF THE INVENTION

The present invention relates to a substance that can emit light by current excitation, and also relates to a photoelectronics device, a light emitting element, and a light emitting device using the substance.

BACKGROUND ART

A light emitting element using an organic compound is an element in which a layer including the organic compound (or organic compound film) emits light by applying an electric field. A structure in which a layer including a luminescent organic compound (light emitting layer) is interposed between a pair of electrodes is a basic structure of the light emitting element. By applying voltage to this element, electrons and holes are transported to the light emitting layer respectively from the pair of electrodes, and current flows. Then, the luminescent organic compound forms an excited state by re-combining those carriers (electrons and holes), and light is emitted when the excited state returns to a grand state.

In such a light emitting element, an organic compound film is usually formed to have a thin thickness below 1 μm. Further, since such a light emitting element is a self-luminous element in which the organic compound film itself emits light, a backlight used for conventional liquid crystal displays is unnecessary. Accordingly, the light emitting element has a great advantage that it can be manufactured to have an ultra thin film thickness and lightweight. Further, in the case of an organic compound film of approximately 100 to 200 nm, time between the injection of carriers and recombination thereof is about several ten nanoseconds considering the carrier mobility of the organic compound film. The time required for light-emission is about 1μ second or less, even if including a process from the recombination of carriers to the emission of light. Thus, an extremely high response speed is also one of the features thereof. In addition, since such a light emitting element is a carrier injection type light emitting element, driving by a direct current voltage is possible, therefore, noise is hardly caused. With respect to a driving voltage, the organic compound film is formed to be a uniform ultra thin film having a thickness of approximately 100 nm, and a material for an electrode is selected so as to reduce a carrier injection barrier to the organic compound film. Further, a hetero structure (here, two-layer structure) is introduced to achieve a sufficient luminance of 100 cd/m$^2$ at 5.5 V (for example, see C. W. Tang and the other, Applied Physics Letters, vol. 51, No. 12, 913-915 (1987)).

In addition to the element characteristics such as the thin thickness and lightweight, the high response speed, and direct-current low-voltage driving, it can also be regarded as one of the great advantages that the light emitting element using an organic compound has wide variation of emission colors. The factor is the multiplicity of the organic compound itself. That is, flexibility that materials of the various emission colors can be developed by molecule design (for example, introducing a substituent) and the like, produces richness in colors. It can be said that the biggest application field of the light emitting element utilizing the richness in colors is a full color flat panel display. Many organic compounds that can emit three primary colors of light, that is, red, green, and blue, exist. Therefore, by patterning thereof, full color can be easily accomplished.

The element characteristics such as the thin thickness and lightweight, the high response speed, and direct-current low-voltage driving as described above can also be regarded as the characteristics that are suitable for a flat panel display. In recent years, as an attempt to further improve luminous efficiency, it is proposed to use not a fluorescent material but a phosphorescent material. In a light emitting element using the organic compound, light is emitted when a molecular exciton returns to the ground state. For the light emission element, luminescence from a singlet excitation state (S*) (fluorescence) and the luminescence from a triplet excitation state (T*) (phosphorescence) are possible. In the case where the fluorescent material is used, only luminescence from S* (fluorescence) contributes to the light emission.

However, it is believed that a statistical generation ratio of S* to T* in the light emitting element is S*:T*=1:3 (for example, see Tetsuo TSUTSUI, Textbook for the 3$^{rd}$ Workshop, Division of Organic Molecular Electronics and Bioelectronics, Japan Society of Applied Physics, P. 31 (1993)). Accordingly, the theoretical limit of the internal quantum efficiency (the ratio of generating photons to injected carrier) in a light emitting element using the fluorescent material is believed to be 25% on the ground of S*:T*=1:3. In other words, in the case of a light emitting element using the fluorescent material, at least 75% of the injected carriers are wasted.

On contrary, it is considered that luminous efficiency is improved (simply by 3 to 4 times) if luminescence from T*, that is, phosphorescence can be utilized. However, in the case of a usual organic compound, luminescence from T* (phosphorescence) is not observed at a room temperature, and normally, only luminescence from S* (fluorescence) is observed. This is because the ground state of an organic compound is normally a singlet ground state (S$_0$), and thus, T*→S$_0$ transition is a forbidden transition and S*→S$_0$ transition is an allowed transition. However, the announcements of a light emitting element that is capable of converting energy released in returning to the ground state from T* (hereinafter referred to as "triplet excitation energy") into luminescence have been given one after another in recent years, and the highness of the luminous efficiency has attracted attention (for example, see Tetsuo TSUTSUI, and eight others, Japanese Journal of Applied Physics, vol. 38, L1502-L1504 (1999)).

A metal complex with iridium as a central metal (hereinafter referred to as "iridium complex") is used as a luminescent material in this reference. It can be said that introducing a third transition series element as the central metal is a feature. These are materials capable of converting a triplet excitation state into luminescence (material capable of emitting phosphorescence) at a room temperature. As shown this reference, the light emitting element using the substance capable of emitting phosphorescence can accomplish higher internal quantum efficiency than conventionally prior art. Then, as the internal quantum efficiency becomes higher, the luminous efficiency ([lm/W]) is improved.

However, as for the Ir complex disclosed in this reference only a complex exhibiting green emission of light is disclosed. Accordingly, at present, a development of a substance that can emit phosphorescence of various colors is desired.

PROBLEMS TO BE SOLVED BY THE INVENTION

In the view of the foregoing problem, it is an object of the present invention to provide a substance that can emit phosphorescence. Further, it is an object of the present invention to provide a light emitting element with favorable color purity. Furthermore, it is an object of the present invention to provide a light emitting device using the light emitting element.

MEANS TO SOLVE THE PROBLEM

The present invention provides an organometallic complex having a structure represented by a following general formula (1).

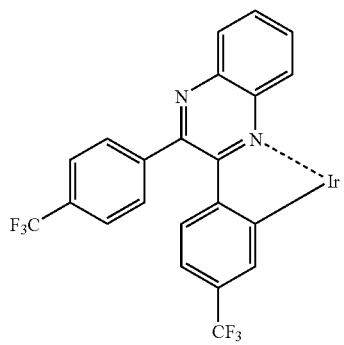

(1)

As the organometallic complex having the structure represented by the general formula (1), an organometallic complex represented by a following general formula (2) can be given,

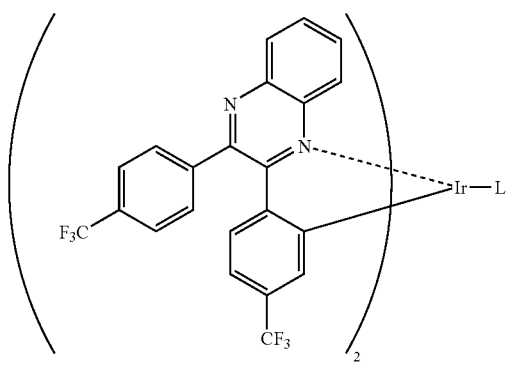

(2)

wherein, L represents any of a monoanionic ligand having a β-diketone structure, a monoanionic bidentate chelate ligand having a carboxyl group, and a monoanionic bidentate chelate ligand having a phenolic hydroxyl group.

In the above structure, it is preferable that the L is a ligand represented by any of structural formulas (3) to (9).

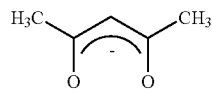

(3)

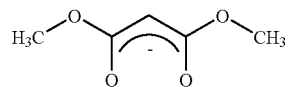

(4)

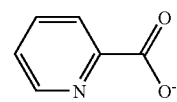

(5)

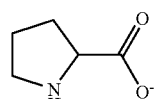

(6)

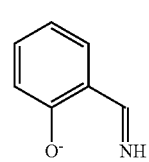

(7)

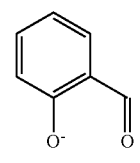

(8)

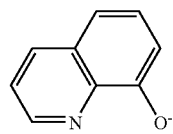

(9)

Further, as the organometallic complex having the structure represented by the general formula (1), an organometallic complex represented by a following structural formula (10) can be given.

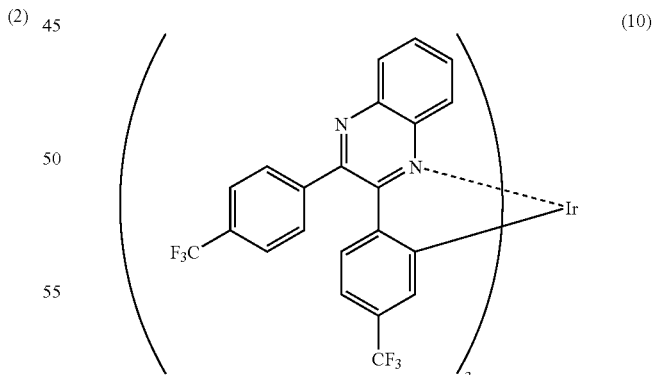

(10)

In addition, an aspect of the present invention is a photoelectronics device that has a feature of containing the organometallic complex represented by any of the above general formulas (1), (2), and the structural formula (10).

Further, another aspect of the present invention is a light emitting element that has a feature of having a layer containing the organometallic complex represented by any of the above general formulas (1), (2), and the structural formula (10) between a pair of electrodes.

Further, another aspect of the present invention is a light emitting element that has a feature of using the organometallic complex represented by any of the above general formulas (1), (2), and the structural formula (10) as a luminescent substance.

Further, another aspect of the present invention is a light emitting element that has a feature of using the organometallic complex represented by any of the above general formulas (1), (2), and the structural formula (10) as a sensitizer for a fluorescent compound.

Further, another aspect of the present invention is a light emitting device that has a feature that a plurality of the light emitting elements is arranged therein.

Further, another aspect of the present invention is a light emitting device that has a feature of using the light emitting element as a pixel.

Further, another aspect of the present invention is an electronic equipment that has a feature of using the light emitting device as a display portion.

EFFECT OF THE INVENTION

In accordance with the present invention, an organometallic complex that can emit phosphorescence can be obtained. In addition, in accordance with the present invention, an organometallic complex that can be used as for a luminescent substance or a sensitizer can be obtained.

A light emitting element that is capable of exhibiting red or reddish light with favorable color purity can be obtained by using the organometallic complex of the present invention as a luminescent substance. In addition, a light emitting element that is capable of emitting light efficiently can be obtained by using the organometallic complex of the present invention as a sensitizer. Further, since the organometallic complex of the present invention includes a trifluoromethyl group that is an electron-withdrawing group, a light emitting element that has a favorable recombination rate can be manufactured.

BEST MODE FOR CARRYING OUT THE INVENTION

Figure 1:
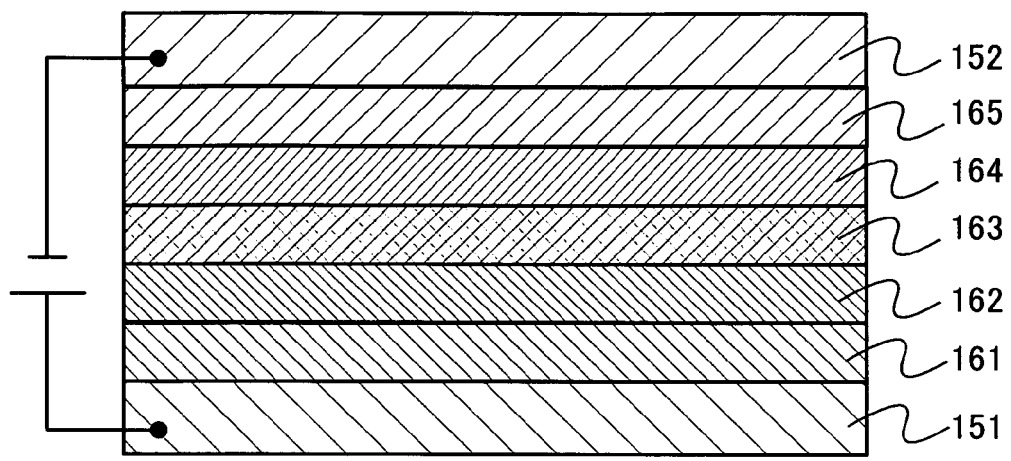
FIG. 1 is an explanatory view of a light emitting element of the present invention.

Embodiment modes of the present invention will hereinafter be described with reference to the accompanying drawings. The present invention can be carried out in many different modes, and it is easily understood by those skilled in the art that modes and details herein disclosed can be modified in various ways without departing from the spirit and the scope of the present invention. It should be noted that the present invention should not be interpreted as being limited to the description of the embodiment modes to be given below.

It is to be noted that when a voltage is applied to a pair of electrodes of a light emitting element of the present invention so that a potential of one electrode thereof is higher than that of the other electrode to generate light, one electrode having a higher potential is referred to as an electrode functioning as an anode, and the other electrode is referred to as an electrode functioning as a cathode.

Embodiment Mode 1

In this embodiment mode, an organometallic complex of the present invention is described.

The organometallic complex of the present invention is an organometallic complex having a structure represented by the following general formula (1).

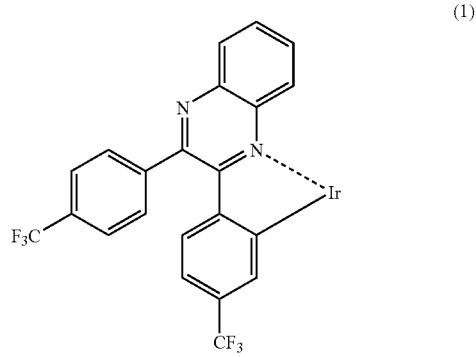

As an organometallic complex having the structure represented by the general formula (1), an organometallic complex represented by the following general formula (2) can be given.

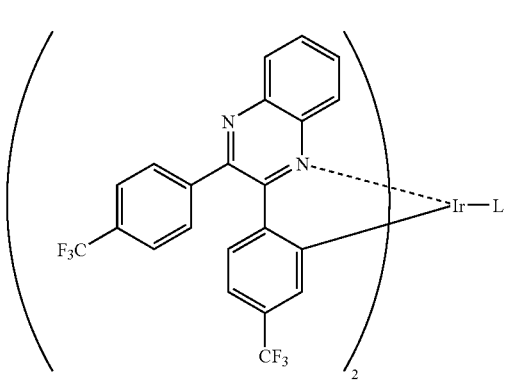

(2)

wherein, L represents any of a monoanionic ligand having a β diketone structure, a monoanionic bidentate chelate ligand having a carboxyl group, and a monoanionic bidentate chelate ligand having a phenolic hydroxyl group.

In the above structures, L preferably represents any of the ligands represented by the structural formulas (3) to (9).

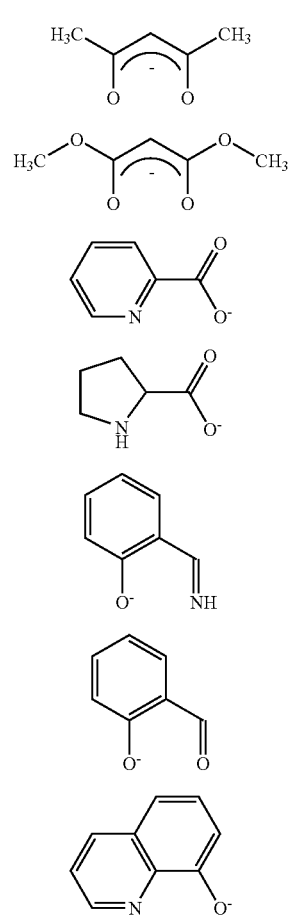

As an organometallic complex having the structure represented by the general formula (1), an organometallic complex represented by the following structural formula (10) can be given.

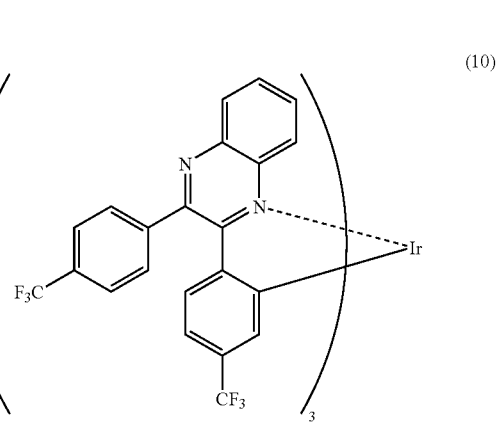

(10)

More specifically, as the organometallic complexes including the structures represented by the general formulas (1), (2), and (10), organometallic complexes represented by structural formulas (11) to (18) can be given.

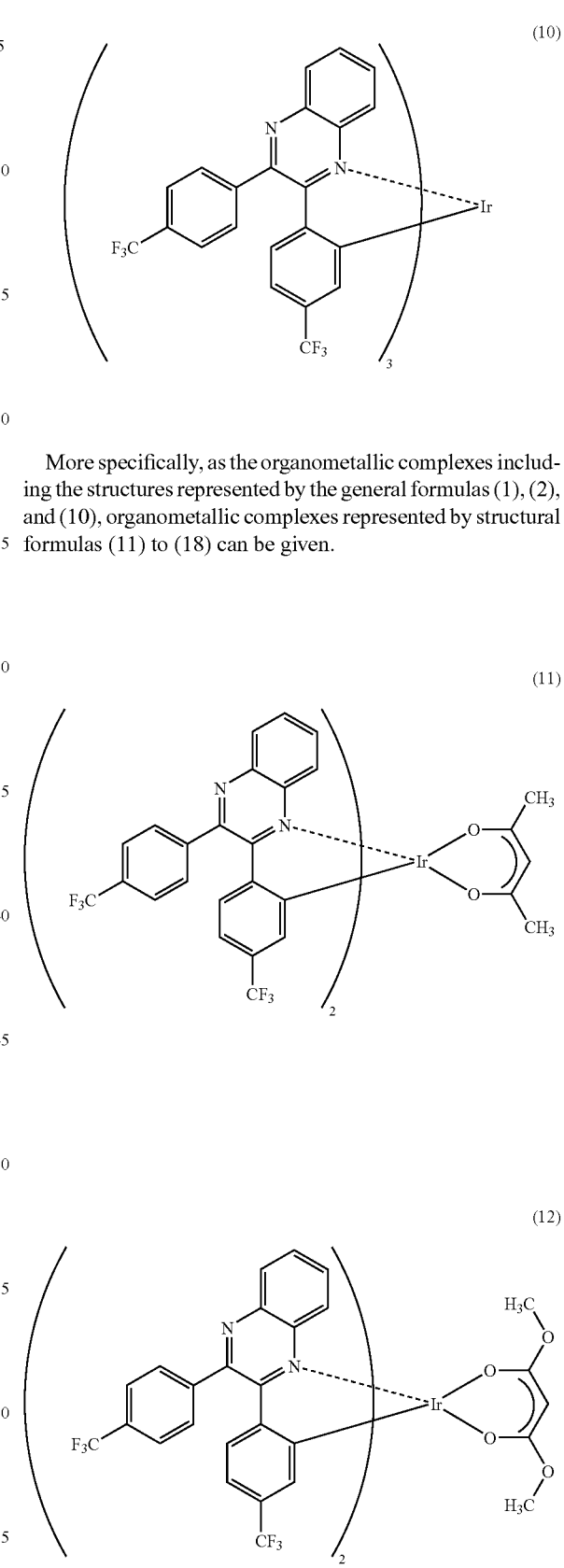

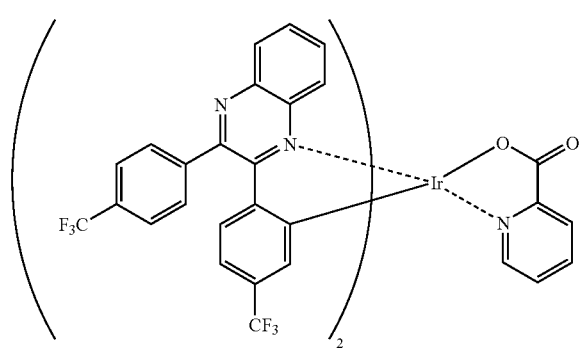

(13)

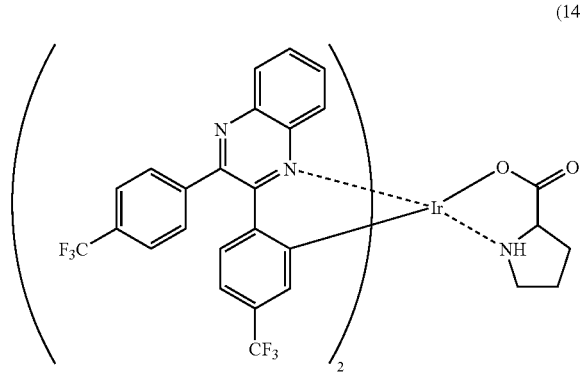

(14)

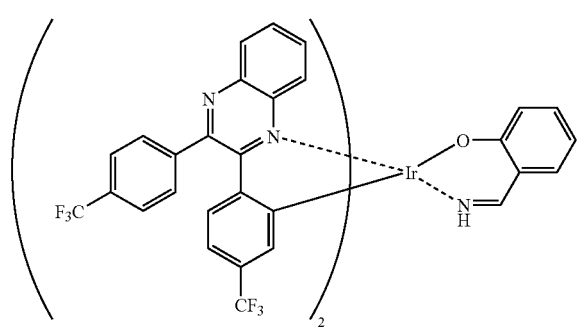

(15)

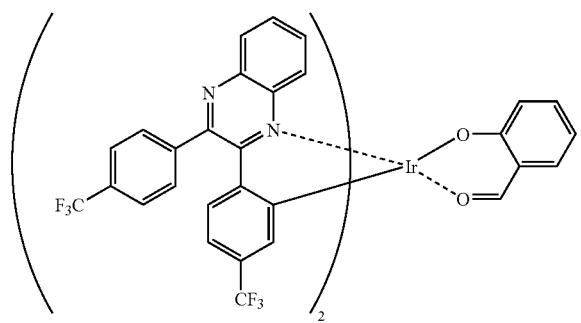

(16)

(17)

(18)

There are a geometrical isomer and a stereoisomer of the organometallic complexes represented by the structural formulas (13) to (17). The organometallic complex of the present invention includes such isomers.

In addition, there are two geometrical isomers of a facial isomer and a meridional isomer in the organometallic complex represented by the structural formula (18). The organometallic complex of the present invention includes such isomers, too.

The foregoing organometallic complex of the present invention can emit phosphorescence. In addition, the organometallic complex of the present invention can be applied to a light emitting element as a luminescent material. In addition, the organometallic complex of the present invention can be applied to a light emitting element as a photosensitizer.

The organometallic complex of the present invention has strong absorption corresponding to triplet MLCT transition, and has comparatively strong absorption over the entire visible light region. Therefore, the organometallic complex of the present invention can be used for a device utilizing absorption of visible light, for example, used for a dye sensitized solar cell as its dye, so that a device with high conversion efficiency can be obtained.

In addition, as for the organometallic complex of the present invention, a difference between the peak of triplet MLCT (Metal to ligand charge transfer) absorption and the peak of an emission spectrum, in other words, a Stokes shift, is small. Therefore, it is suggested that a molecule in an excited state be stable. That is, the organometallic complex of the present invention is a preferable material for a photoelectronics device such as a dye sensitized solar cell and a light emitting element because a molecule in the triplet MLCT excited state is stable. In addition, a dye sensitized solar cell is a solar cell in which an oxide semiconductor and a dye are used in substitution for a p-n junction to generate electricity.

In addition, a half width of an emission spectrum of the organometallic complex of the present invention is comparatively narrow, and a sharp peak is represented. In other words, the organometallic complex of the present invention can realize light emission with favorable color purity.

The organometallic complex of the present invention can be used for various photoelectronics devices such as a dye sensitized solar cell without being restricted to a light emitting element.

Embodiment Mode 2

An organometallic complex of the present invention can be obtained by an ortho metalation reaction of a ligand. For example, an organometallic complex having a ligand represented by a following structural formula (19) is obtained by an ortho metalation reaction of the ligand represented by the following structural formula (19). In this mode, a synthesis method of the organometallic complex represented by the foregoing general formula (2), in which the ligand represented by the structural formula (19) is used is explained.

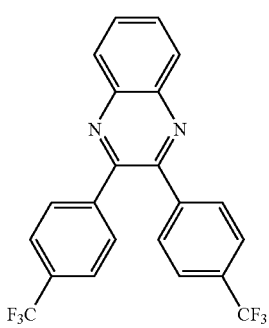

(19)

It is to be noted that, for example, the ligand represented by the structural formula (19) can be synthesized as shown in a following synthesis scheme (A-1).

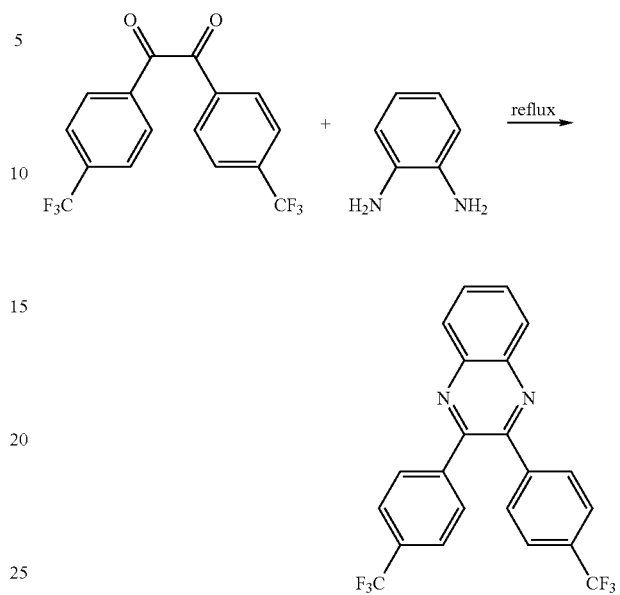

(A-1)

The obtained ligand represented by the structural formula (19) is used to synthesize the organometallic complex of the present invention. As the reaction (an ortho metalation reaction), the following synthesis method may be used.

The organometallic complex of the present invention uses iridium as a central metal. Therefore, in the case of synthesizing the organometallic complex of the present invention, iridium chloride hydrate which is a central metal material, and the ligand of the structural formula (19) are mixed and refluxed in a nitrogen atmosphere to synthesize a chlorine-bridged binuclear complex first (a following synthesis scheme (A-2)). Next, the chlorine-bridge is cut by the ligand L by mixing the obtained binuclear complex and the ligand L and refluxing them in a nitrogen atmosphere so as to obtain the organometallic complex of the present invention (a following synthesis scheme (A-3)). Here, the ligand L is not restricted in particular, but preferably is the ligand represented by any of the structural formulas (3) to (9).

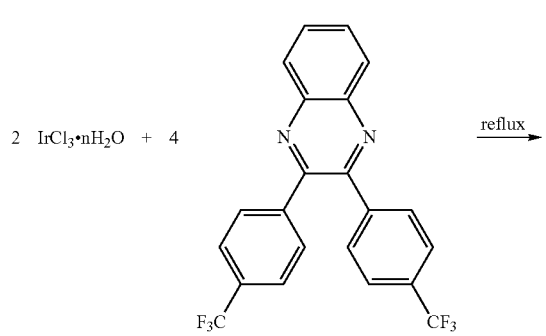

(A-2)

-continued

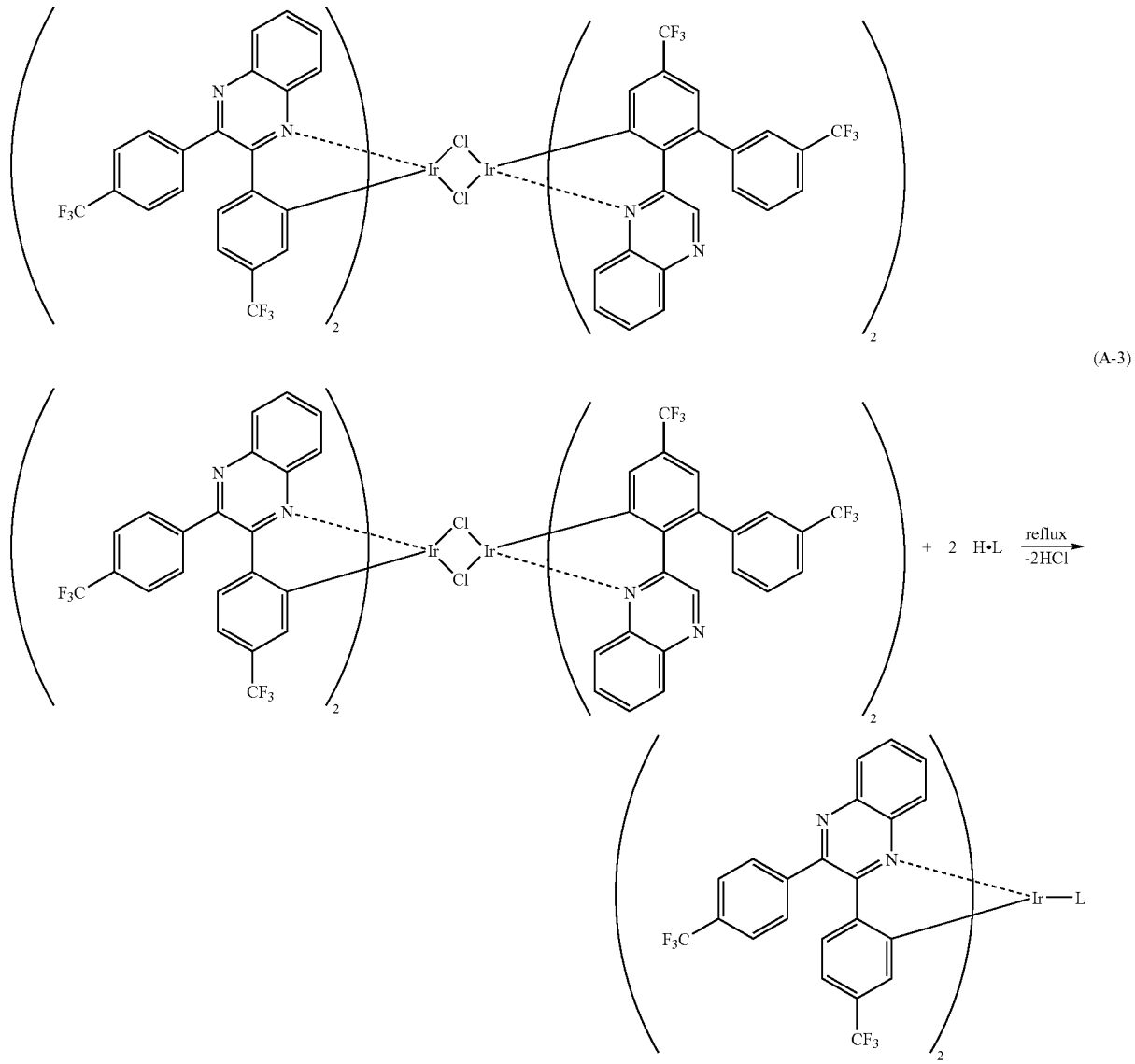

(A-3)

In addition, in the organometallic complex represented by the general formula (2), the organometallic complex of the present invention represented by the structural formula (10) can be obtained by substituting the monoanionic ligand L coordinated with iridium by the ligand represented by the structural formula (19).

It is to be noted that the synthesis method of the organometallic complex of the present invention is not restricted to the foregoing synthesis method.

Embodiment Mode 3

A mode of a light emitting element which has the organometallic complex of the present invention as a luminescent substance is explained with reference to FIG. 1.

As shown in FIG. 1, a light emitting element has a light emitting layer 163 formed between a first electrode 151 and a second electrode 152. The light emitting layer 163 has the organometallic complex of the present invention including the structure represented by any of the general formulas (1) and (2) and the structural formula (10).

In such a light emitting element, a hole injected from the first electrode 151 side and an electron injected from the second 152 electrode side recombine with each other in the light emitting layer 163 to bring the organometallic complex to an excited state. And when the organometallic complex of the present invention in the excited state returns to a ground state, it emits light. As thus described, the organometallic complex of the present invention functions as a luminescent substance. In the light emitting element of this mode, the first electrode 151 functions as an anode and the second electrode 152 functions as a cathode.

The light emitting layer 163 is preferably a layer formed from a substance which has a larger energy gap than that of the organometallic complex of the present invention, in which the organometallic complex of the present invention is dispersedly contained. Thus, quenching of light emitted from the organometallic complex of the present invention caused depending on the concentration can be prevented. It is to be noted that the energy gap indicates the energy gap between a LUMO level and a HOMO level.

The substance used for dispersing the organometallic complex of the present invention is not particularly restricted. In addition to a compound having an arylamine skeleton such as 2,3-bis(4-diphenylaminophenyl)quinoxaline (abbreviation: TPAQn) or 4,4'-bis[N-(1-naphthyl)-N-phenylamino]-biphenyl (abbreviation: α-NPD), a carbazole derivative such as 4,4'-bis(N-carbazolyl)biphenyl (abbreviation: CBP) or 4,4', 4"-tris(N-carbazolyl)-triphenylamine (abbreviation: TCTA), or a metal complex such as bis[2-(2-hydroxyphenyl)-pyridinato]zinc (abbreviation: $Znpp_2$), bis[2-(2-hydroxyphenyl)-benzoxazolato]zinc (abbreviation: ZnBOX), or tris(8-quinolinolato)aluminum (abbreviation: $Alq_3$), or the like is preferably used.

Since the organometallic complex of the present invention has a trifluoromethyl group which is an electron-withdrawing substituent, a light emitting element with favorable color purity and quantum efficiency can be obtained. In addition, a light emitting element with high recombining efficiency can be obtained.

Although the first electrode 151 is not particularly restricted, the first electrode 151 is preferably formed by using a substance which has a large work function when the first electrode 151 functions as an anode as in this mode. Specifically, in addition to indium tin oxide (ITO), indium tin oxide containing silicon oxide, and indium oxide containing zinc oxide at 2 to 20 wt %; gold (Au), platinum (Pt), nickel (Ni), tungsten (W), chromium (Cr), molybdenum (Mo), iron (Fe), cobalt (Co), copper (Cu), palladium (Pd), or the like can be used. The first electrode 151 can be formed by, for example, a sputtering method, a vapor deposition method, or the like.

Further, although the second electrode 152 is not particularly restricted, the second electrode 152 is preferably formed from a substance which has a small work function when the second electrode 152 functions as a cathode as in this mode. Specifically, aluminum or the like containing an alkali metal or an alkali-earth metal such as lithium (Li), magnesium, or the like can be used. The second electrode 152 can be formed by, for example, a sputtering method, a vapor deposition method, or the like.

In order to extract emitted light to outside, one or both the first electrode 151 and the second electrode 152 is/are preferably an electrode formed of a conductive film of indium tin oxide or the like which can transmit visible light or an electrode formed to have a thickness of several to several tens nm so as to transmit visible light.

In addition, a hole transporting layer 162 may be provided between the first electrode 151 and the light emitting layer 163 as shown in FIG. 1. Here, a hole transporting layer is a layer which has a function for transporting holes injected from the first electrode 151 to the light emitting layer 163. The hole transporting layer 162 is provided to keep the first electrode 151 away from the light emitting layer 163 in this way; thus, quenching of light due to a metal can be prevented.

The hole transporting layer 162 is not particularly restricted, and a layer formed from, for example, an aromatic amine compound (that is, a compound having a benzene ring-nitrogen bond) such as 4,4'-bis[N-(1-naphthyl)-N-phenyl-amino]-biphenyl (abbreviation: α-NPD), 4,4'-bis[N-(3-methylphenyl)-N-phenyl-amino]-biphenyl (abbreviation: TPD), 4,4',4"-tris(N,N-diphenyl-amino)-triphenylamine (abbreviation: TDATA), or 4,4',4"-tris[N-(3-methylphenyl)-N-phenyl-amino]-triphenylamine abbreviation: MTDATA) can be used.

In addition, the hole transporting layer 162 may be a layer which has a multilayer structure formed by combining two or more layers each containing the substance mentioned above.

Further, an electron transporting layer 164 may be provided between the second electrode 152 and the light emitting layer 163 as shown in FIG. 1. Here, the electron transporting layer is a layer which has a function for transporting electrons injected from the second electrode 152 to the light emitting layer 163. The electron transporting layer 164 is provided to keep the second electrode 152 away from the light emitting layer 163 in this way; thus, quenching of light due to a metal can be prevented.

The electron transporting layer 164 is not particularly restricted, and a layer formed from, for example, a metal complex having a quinoline skeleton or a benzoquinoline skeleton, such as tris(8-quinolinolato)aluminum (abbreviation: $Alq_3$), tris(5-methyl-8-quinolinolato)aluminum (abbreviation: $Almq_3$), bis(10-hydroxybenzo[h]quinolinato)beryllium (abbreviation: $BeBq_2$), or bis(2-methyl-8-quinolinolato)-4-phenylphenolato-aluminum (abbreviation: BAlq) can be used. In addition, a layer formed from, for example, a metal complex having an oxazole-based ligand or a thiazole-based ligand such as bis[2-(2-hydroxyphenyl)-benzoxazolato]zinc (abbreviation: $Zn(BOX)_2$) or bis[2-(2-hydroxyphenyl)-benzothiazolato]zinc (abbreviation: $Zn(BTZ)_2$) may be used. Further, a layer formed from 2-(4-biphenylyl)-5-(4-tert-butylphenyl)-1,3,4-oxadiazole (abbreviation: PBD), 1,3-bis[5-(p-tert-butylphenyl)-1,3,4-oxadiazole-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproin (abbreviation: BCP; 2,9-Dimethyl-4,7-diphenyl-1,10-phenanthroline), or the like may be used.

In addition, the electron transporting layer 164 may be a layer that has a multilayer structure formed by combining two or more layers each containing the substance mentioned above.

Further, a hole injecting layer 161 may be provided between the first electrode 151 and the hole transporting layer 162 as shown in FIG. 1. Here, a hole injecting layer is a layer that has a function for assisting injection of holes from an electrode functioning as an anode to the hole transporting layer 162. It is to be noted that injection of the holes to the light emitting layer may be assisted by providing a hole injecting layer between the electrode functioning as an anode and the light emitting layer when the hole transporting layer is not particularly provided.

The hole injecting layer 161 is not particularly restricted, and a layer formed from, for example, metal oxide such as molybdenum oxide ($MoO_x$), vanadium oxide ($VO_x$), ruthenium oxide ($RuO_x$), tungsten oxide ($WO_x$), manganese oxide ($MnO_x$) or the like. In addition, the hole injecting layer 161 can be formed from phthalocyanine (abbreviation: $H_2Pc$) or a phthalocyanine based compound such as copper phthalocyanine (abbreviation: CuPc), a polymer such as a poly(ethylenedioxythiophene)/poly(styrene sulfonate) aqueous solution (PEDOT/PSS), or the like.

A composite material which is formed by composition of an organic compound and an inorganic compound may be used for the hole injecting layer and the hole transporting layer. In particular, a composite material having an organic compound and an inorganic compound which has an electron accepting property to the organic compound is excellent in a hole injecting property and a hole transporting property since electrons are transferred between the organic compound and the inorganic compound to generate holes. In this case, the organic compound is preferably a material excellent in transporting the generated holes. Specifically, the foregoing aromatic amine-based organic compound is preferable. An inorganic compound is preferably a substance showing an electron accepting property to the organic compound, and specifically transition metal oxide is preferable. For example, metal oxide such as titanium oxide ($TiO_x$), vanadium oxide ($VO_x$), molybdenum oxide ($MoO_x$), tungsten oxide ($WO_x$), rhenium oxide ($ReO_x$), ruthenium oxide ($RuO_x$), chromium oxide ($CrO_x$), zirconium oxide ($ZrO_x$), hafnium oxide ($HfO_x$), tantalum oxide ($TaO_x$), silver oxide ($AgO_x$), or manganese oxide ($MnO_x$) can be used.

Further, an electron injecting layer 165 may be provided between the second electrode 152 and the electron transporting layer 164 as shown in FIG. 1. Here, an electron injecting layer is a layer which has a function for assisting injection of electrons from the electrode functioning as a cathode to the electron transporting layer 164. It is to be noted that injection of the electrons to the light emitting layer may be assisted by providing an electron injecting layer between the electrode functioning as a cathode and the light emitting layer when the electron transporting layer is not particularly provided.

The electron injecting layer 165 is not particularly restricted, and a layer formed from, for example, a compound of an alkali metal or an alkali-earth metal such as lithium fluoride (LiF), cesium fluoride (CsF), calcium fluoride ($CaF_2$), or the like can be used. In addition, a layer in which a substance having a high electron transporting property is mixed with an alkali metal or an alkali-earth metal such as magnesium or lithium such as $Alq_3$, 4,4-bis(5-methylbenzoxazol-2-yl)stilbene (BzOs), or the like can also be used as the electron injecting layer 165.

A composite material which is formed by composition of an organic compound and an inorganic compound may be used for the electron injecting layer and the electron transporting layer. In particular, a composite material having an organic compound and an inorganic compound which has an electron donating property to the organic compound is excellent in an electron injecting property and an electron transporting property since electrons are transferred between the organic compound and the inorganic compound to generate electrons. In this case, the organic compound is preferably a material excellent in transporting the generated electrons. Specifically, the foregoing materials which can be used for the electron transporting layer are preferable. The inorganic compound is preferably a substance showing an electron donating property to the organic compound, and specifically an alkali metal oxide or an alkali-earth metal oxide is preferable. For example, lithium oxide, calcium oxide, barium oxide, or the like can be used.

In the foregoing light emitting element of the present invention, each of the hole injecting layer 161, the hole transporting layer 162, the light emitting layer 163, the electron transporting layer 164, and the electron injecting layer 165 may be formed by any method, for example, a vapor deposition method, an inkjet method, a coating method, or the like. In addition, the first electrode 151 or the second electrode 152 may be formed by any method, for example, a sputtering method, a vapor deposition method, or the like.

A light emitting element of the present invention described above can emit red light with favorable color purity because of the use of the organometallic complex of the present invention. In addition, since the light emitting element of the present invention can emit phosphoresce, the luminous efficiency is preferable. A light emitting element including a layer formed from a quinoxaline derivative in which the organometallic complex of the present invention is dispersedly contained emits light particularly efficiently.

Embodiment Mode 4

The light emitting element of the present invention may have a plurality of light emitting layers. For example, white light can be obtained by providing a plurality of light emitting layers and mixing light emitted from each of the light emitting layers. In this mode, alight emitting element having a plurality of light emitting layers is described with reference to FIGS. 2 and 3.

Figure 2:
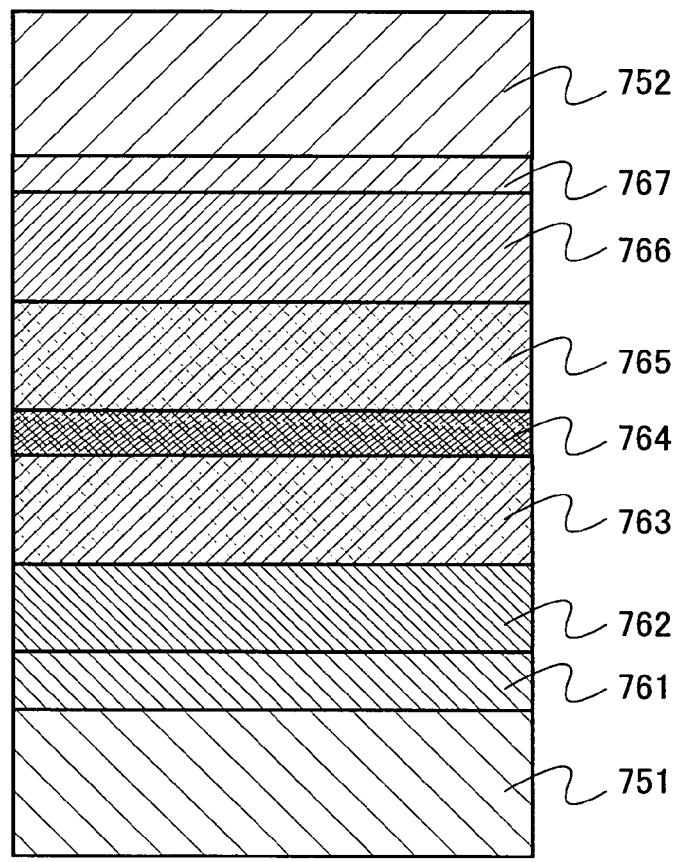
FIG. 2 is an explanatory view of a light emitting element of the present invention.

In FIG. 2, a first light emitting layer 763 and a second light emitting layer 765 are provided between a first electrode 751 and a second electrode 752. A partition layer 764 is preferably formed between the first light emitting layer 763 and the second light emitting layer 765.

When voltage is applied so that the potential of the second electrode 752 is higher than the potential of the first electrode 751, current flows between the first electrode 751 and the second electrode 752, and holes and electrons are recombined in the first light emitting layer 763, the second light emitting layer 765, or the partition layer 764. Generated excitation energy transfers to both the first light emitting layer 763 and the second light emitting layer 765 through the partition layer 764 to bring each of a first luminescent material contained in the first light emitting layer 763 and a second luminescent material contained in the second light emitting layer 765 to an excited state. Then, the first and second luminescent substances in the excited state emit light when returning to the ground state.

The first light emitting layer 763 contains a luminescent substance typified by a fluorescent substance such as perylene, 2,5,8,11-tetra-tert-butylperylene (TBP), 4,4'-bis[2-diphenylvinyl]biphenyl (DPVBi), 4,4'-bis[2-(N-ethylcarbazole-3-yl)vinyl]biphenyl (BCzVBi), bis(2-methyl-8-quinolinolato)-4-phenylphenolato-aluminum (BAlq), or bis(2-methyl-8-quinolinolato)-chlorogallium ($Gamq_2Cl$), or a phosphorescent substance such as bis[2-(3,5-bis(trifluoromethyl)phenyl)pyridinato-N,$C^{2'}$]iridium (III)picolinate (Ir($CF_3$ppy)$_2$(pic)), bis[2-(4,6-difluorophenyl)pyridinato-N,$C^{2'}$]iridium(III)acetylacetonate (FIr(acac)), or bis[2-(4,6-difluorophenyl)pyridinato-N,$C^{2'}$]iridium(III)picolinate (FIr(pic)), from which light emission with a peak at 450 to 510 nm in an emission spectrum can be obtained. In addition, the second light emitting layer 765 contains the organometallic complex of the present invention functioning as a luminescent substance, from which light emission with a peak at 580 to 680 nm in an emission spectrum can be obtained. Then, the color of light emitted from the first light emitting layer 763 and the color of light emitted from the second light emitting layer 765 are emitted to outside through one or both the first electrode 751 and the second electrode 752. Light emitted to outside is visually mixed to be visually recognized as white light.

The first light emitting layer 763 is preferably a layer formed from a substance (first host) which has a larger energy gap than that of a luminescent substance, in which the luminescent substance which can emit light of 450 to 510 nm is dispersedly contained; or a layer formed from a luminescent substance which can emit light of 450 to 510 nm. As the first host, in addition to the foregoing α-NPD, CBP, TCTA, $Znpp_2$, and ZnBOX, 9,10-di(2-naphthyl)anthracene (abbreviation: DNA), 9,10-di(2-naphthyl)-2-tert-butylanthracene (abbreviation: t-BuDNA), and the like can be used. Further, the second light emitting layer 765 is preferably a layer formed from a substance (second host) which has a larger energy gap than that of the organometallic complex of the present invention, in which the organometallic complex of the present invention is dispersedly contained. As the second host, TPAQn, α-NPD, CBP, TCTA, Znpp$_2$, ZnBOX, Alq$_3$, or the like can be used. Further, the partition layer 764 is preferably formed so that energy generated in the first light emitting layer 763, the second light emitting layer 765, or the partition layer 764 can transfer to both the first light emitting layer 763 and the second light emitting layer 765, and formed to have a function for preventing the energy from transferring only one of the first light emitting layer 763 and the second light emitting layer 765. Specifically, the partition layer 764 can be formed from TPAQn, α-NPD, CBP, TCTA, Znpp$_2$, ZnBOX, or the like. As described above, by providing the partition layer 764, a defect that high emission intensity from only one of the first light emitting layer 763 and the second light emitting layer 765 makes it impossible to obtain white light can be prevented.

The luminescent substance contained in each of the first light emitting layer 763 and the second light emitting layer 765 is not particularly restricted. Either of the light emitting layers may contain the organometallic complex of the present invention.

In this mode, the light emitting element provided with the two light emitting layers as shown in FIG. 2 is described. However, the number of light emitting layers is not restricted to two, and for example, three light emitting layers may be used. Light emitted from each of the light emitting layers may be mixed to be visually recognized as white light.

An electron transporting layer 762 may be provided between the first light emitting layer 763 and the first electrode 751 as shown in FIG. 2. An electron injecting layer 761 may be provided between the electron transporting layer 762 and the first electrode 751 in addition to the electron transporting layer 762. Further, a hole transporting layer 766 may be provided between the second light emitting layer 765 and the second electrode 752 as shown in FIG. 2. Furthermore, a hole injecting layer 767 may be provided between the hole transporting layer 766 and the second electrode 752.

Other than the light emitting element described with reference to FIG. 2, a light emitting element shown in FIG. 3 may be used.

Figure 3:
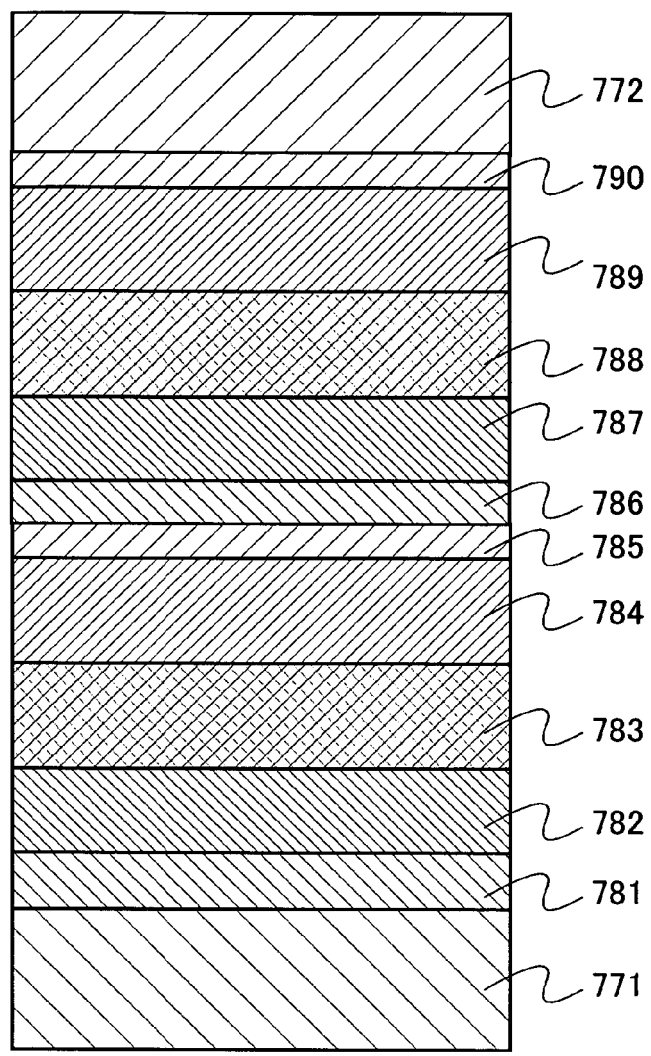
FIG. 3 is an explanatory view of a light emitting element of the present invention.

The light emitting element shown in FIG. 3 has a first light emitting layer 783 and a second light emitting layer 788 between a first electrode 771 and a second electrode 772. A first layer 785 and a second layer 786 are provided between the first light emitting layer 783 and the second light emitting layer 788.

The first layer 785 is a layer which generates holes, and the second layer 786 is a layer which generates electrons. When voltage is applied so that the potential of the second electrode 772 is higher than the that of the first electrode 771, electrons injected from the first electrode 771 side and holes injected from the first layer 785 side are recombined in the first light emitting layer 783, and a luminescent substance contained in the first light emitting layer 783 emits light. Further, holes injected from the second electrode side and electrons injected from the second layer 786 are recombined in the second light emitting layer 788, and a luminescent substance contained in the second light emitting layer 788 emits light.

The organometallic complex of the present invention is contained in the first light emitting layer 783 so as to function as the luminescent substance and light emission with a peak of 580 to 680 nm in light emission spectrum can be obtained from the first light emitting layer 783. In addition, the second light emitting layer 788 contains a luminescent substance typified by a fluorescent substance such as perylene, TBP, DPVBi, BCzVBi, BAlq, or Gamq$_2$Cl; or a phosphorescent substance such as Ir(CF$_3$ppy)$_2$(pic), FIr(acac), or FIr(pic) so that light emission with a peak at 450 to 510 nm in a light emission spectrum can be obtained. Light emitted from the first light emitting layer 783 and the second light emitting layer 788 is extracted from one or both the first electrode 771 and the second electrode 772. Then, the light emitted from both of the light emitting layers is visually mixed to be visually recognized as white light.

In the first light emitting layer 783, the organometallic complex of the present invention is preferably contained so as to be dispersed in the second host in Embodiment Mode 4. The second light emitting layer 788 is preferably formed similarly to the first light emitting layer 763 in Embodiment Mode 4.

The first layer 785 preferably contains a substance which transports more holes than electrons, which contains a substance having an electron accepting property to the substance. As the substance which transports more holes than electrons, the same substance as that is used for forming a hole transporting layer may be used. In addition, as the substance which has an electron accepting property to the substance which transports more holes than electrons, molybdenum oxide, vanadium oxide, 7,7,8,8-tetracyanoquinodimethane (abbreviation: TCNQ), 2,3,5,6-tetrafluoro-7,7,8,8-tetracyanoquinodimethane (abbreviation: F$_4$-TCNQ), or the like can be used.

The second layer 786 preferably contains a substance which transports more electrons than holes, which contains a substance having an electron donating property to the substance. As the substance which transports more electrons than holes, the same substance as that is used for forming an electron transporting layer may be used. In addition, as the substance having an electron donating property to the substance which transports more electrons than holes, an alkali metal such as lithium or cesium, an alkaline-earth metal such as magnesium or calcium, a rare-earth metal such as erbium or ytterbium, or the like can be used.

An electron transporting layer 782 may be provided between the first light emitting layer 783 and the first electrode 771 as shown in FIG. 3. In addition, an electron injecting layer 781 may be provided between the electron transporting layer 782 and the first electrode 771. A hole transporting layer 784 may be provided between the first light emitting layer 783 and the first layer 785. A hole transporting layer 789 may be provided between the second light emitting layer 788 and the second electrode 772. A hole injecting layer 790 may be provided between the hole transporting layer 789 and the second electrode 772. An electron transporting layer 787 may be provided between the second light emitting layer 788 and the second layer 786.

In addition, in this mode, the light emitting element provided with the two light emitting layers as shown in FIG. 3 is described. However, the number of light emitting layers is not restricted to two, and for example, three light emitting layers may be used. Light emitted from each of the light emitting layers may be mixed to be visually recognized as white light.

Embodiment Mode 5

A mode of a light emitting element using the organometallic complex of the present invention as a sensitizer is explained with reference to FIG. 4.

Figure 4:
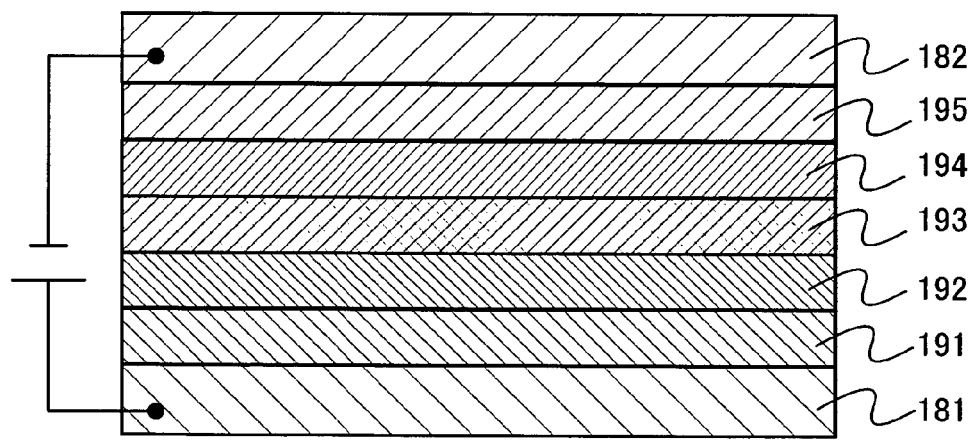
FIG. 4 is an explanatory view of a light emitting element of the present invention.

FIG. 4 shows a light emitting element having a light emitting layer 193 between a first electrode 181 and a second electrode 182. The light emitting layer 193 contains the organometallic complex having any of the structures represented by the general formulas (1), (2), and the structural formula

(10) of the present invention and a fluorescent compound capable of providing light emission of a longer wavelength than the organometallic complex of the present invention. Here, the fluorescent compound is a substance that emits fluorescent light when returning to a ground state from an excited state.

In such a light emitting element, holes injected from the first electrode 181 side and electrons injected from the second electrode 182 side are recombined in the light emitting layer 193 to bring the fluorescent compound to an excited state. Then, light is emitted when the fluorescent compound in the excited state returns to the ground state. In this case, the organometallic complex of the present invention acts as a sensitizer for the fluorescent compound to amplify the number of fluorescent compounds in the singlet excited state. As described above, a light emitting element with favorable luminous efficiency can be obtained by using the organometallic complex of the present invention as a sensitizer. It is to be noted that the first electrode 181 functions as an anode and the second electrode 182 functions as a cathode in the light emitting element in this mode.

Here, the light emitting layer 193 is preferably a layer formed from a substance which has a larger energy gap than the organometallic complex of the present invention, in which the organometallic complex of the present invention and a fluorescent compound are dispersedly contained. Thus deactivation of the exciton of the organometallic complex of the present invention depending on the concentration can be prevented. It is to be noted that an energy gap indicates an energy gap between a LUMO level and a HOMO level.

Here, the fluorescent compound is not particularly restricted, and a compound which shows red to infrared light emission such as magnesium phthalocyanine or phthalocyanine is preferable.

In addition, the substance used for dispersing the organometallic complex of the present invention and the fluorescent compound is not particularly restricted, and the substance which can be used for dispersing the organometallic complex of the present invention as described in Embodiment Mode 3, or the like can be used.

The first electrode and the second electrode are not particularly restricted, and the same substances as those used for the first electrode 151 and second electrode 152 described in Embodiment Mode 3 can be used.

A hole transporting layer 191, a hole injecting layer 192, and the like may be provided between the first electrode 181 and the light emitting layer 193 as shown in FIG. 4. An electron transporting layer 194, an electron injecting layer 195, and the like may be provided also between the second electrode 182 and the light emitting layer 193.

For the hole injecting layer 191, the hole transporting layer 192, the electron transporting layer 194, and the electron injecting layer 195, the same materials as those for the hole injecting layer 161, the hole transporting layer 162, the electron transporting layer 164, and the electron injecting layer 165 described in Embodiment Mode 3 can be used, respectively. In addition, another functional layer and the like which has a different function from the hole injecting layer 191, the hole transporting layer 192, the electron transporting layer 194, and the electron injecting layer 195 may be provided.

The foregoing light emitting element can be obtained by using the organometallic complex of the present invention as a sensitizer.

Embodiment Mode 6

Since a light emitting element having the organometallic complex of the present invention emits light with a favorable color, a light emitting device which has a function for displaying images with favorable colors can be obtained by using the light emitting element of the present invention as a pixel. In addition, since the light emitting element of the present invention can emit light efficiently, a light emitting device with low power consumption can be obtained by applying the light emitting element of the present invention as a pixel or the like.

In this mode, a circuit structure and a driving method of a light emitting device having a display function is described with reference to FIGS. 5 to 8.

Figure 5:
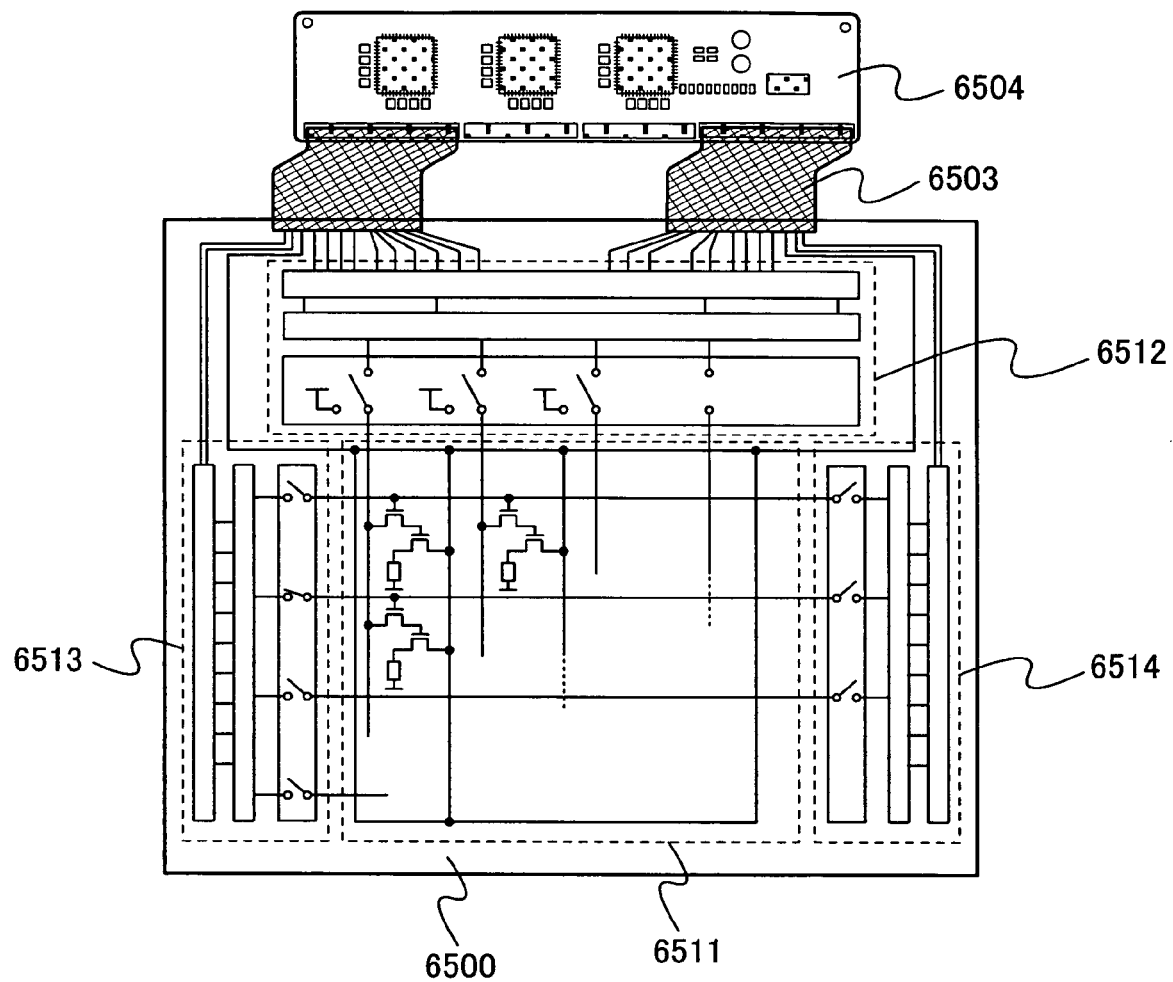
FIG. 5 is an explanatory view of a light emitting device of the present invention.

FIG. 5 is a top schematic view of a light emitting device to which the present invention is applied. In FIG. 5, a pixel portion 6511, a source signal line driver circuit 6512, a writing gate signal line driver circuit 6513, and an erasing gate signal line driver circuit 6514 are provided over a substrate 6500. Each of the source signal line driver circuit 6512, the writing gate signal line driver circuit 6513, and the erasing gate signal line driver circuit 6514 is connected to an FPC (flexible printed circuit) 6503, which is an external input terminal, through a group of wirings. Further, each of the source signal line driver circuit 6512, the writing gate signal line driver circuit 6513, and the erasing gate signal line driver circuit 6514 receives signals such as a video signal, a clock signal, a start signal, a reset signal, and the like from the FPC 6503. A printed wiring board (PWB) 6504 is attached to the FPC 6503. It is to be noted that it is not always necessary to provide the driver circuit portion and the pixel portion 6511 over one substrate as described above. For example, the driver circuit portion may be provided outside the substrate by using an IC chip mounted over the FPC over which a wiring pattern is formed (TCP) or the like.

In the pixel portion 6511, a plurality of source signal lines extending in columns are arranged in rows. In addition, current supply lines are arranged in rows. Further, in the pixel portion 6511, a plurality of gate signal lines extending in rows are arranged in columns. Furthermore, in the pixel portion 6511, a plurality of sets of circuits each including a light emitting element is arranged.

Figure 6:
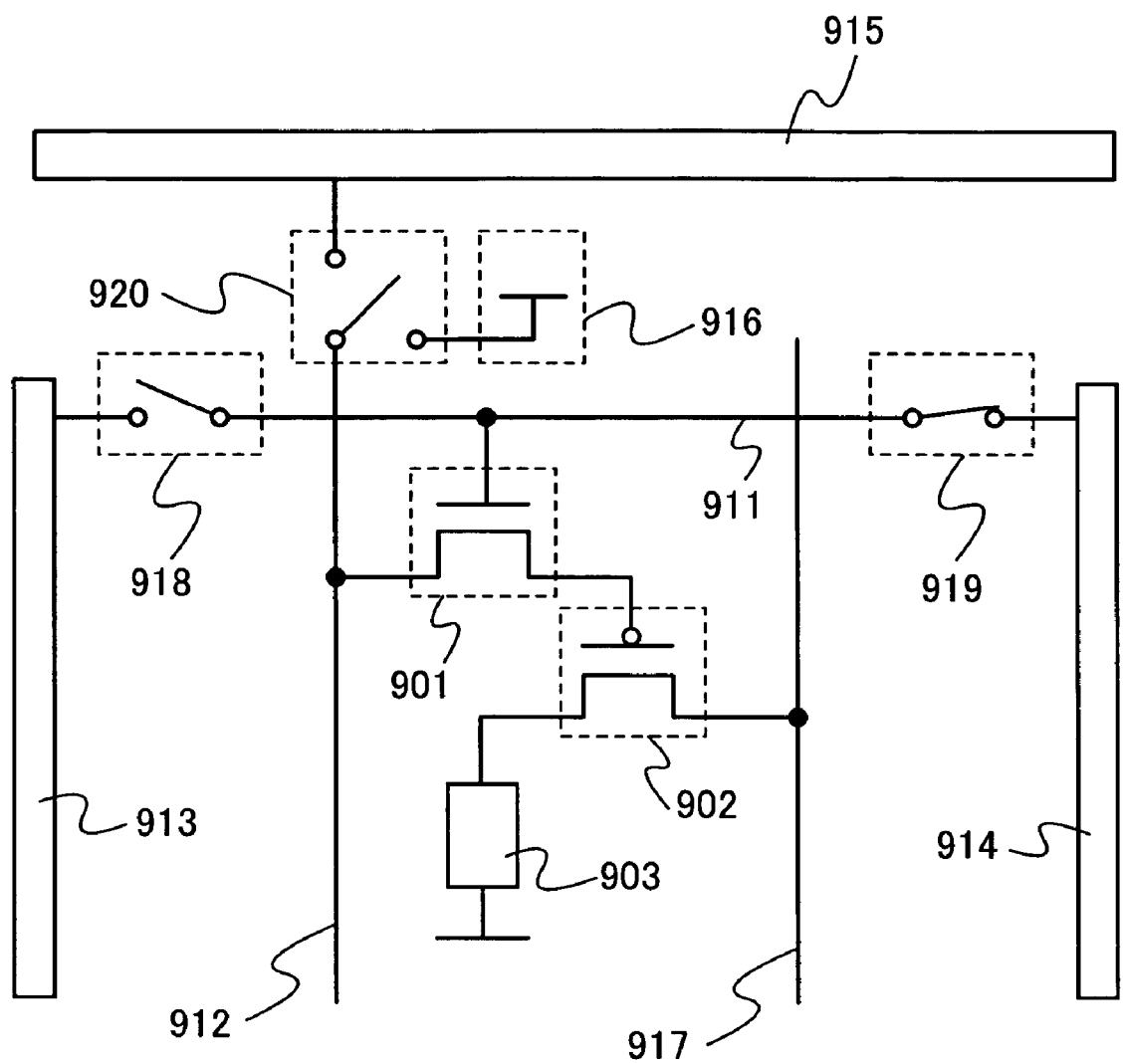
FIG. 6 is an explanatory view of a circuit in a light emitting device of the present invention.

FIG. 6 is a diagram showing a circuit for operating one pixel. The circuit shown in FIG. 6 includes a first transistor 901, a second transistor 902, and a light emitting element 903.

Each of the first transistor 901 and the second transistor 902 is a three-terminal element including a gate electrode, a drain region, and a source region, and has a channel region between the drain region and the source region. Here, since a source region and a drain region are switched with each other in accordance with a structure or operating conditions of a transistor, it is difficult to identify which one is the source region or the drain region. Consequently, in this mode, electrodes connected to the regions which function as a source or a drain are respectively referred to as a first electrode and a second electrode.

A gate signal line 911 and a writing gate signal line driver circuit 913 are provided so as to be electrically connected or disconnected by a switch 918. The gate signal line 911 and an erasing gate signal line driver circuit 914 are provided so as to be electrically connected or disconnected by a switch 919. A source signal line 912 is provided so as to be electrically connected to either of a source signal line driver circuit 915 or a power source 916 by a switch 920. Further, a gate electrode of the first transistor 901 is electrically connected to the gate signal line 911. The first transistor has a first electrode electrically connected to the source signal line 912 and a second electrode electrically connected to a gate electrode of the second transistor 902. The second transistor 902 has a first electrode electrically connected to a current supply line 917 and a second electrode electrically connected to one electrode in the light emitting element 903. It is to be noted that the switch 918 may be included in the writing gate signal line driver circuit 913. The switch 919 may be included in the erasing gate signal line driver circuit 914. The switch 920 may be included in the source signal line driver circuit 915.

Figure 7:
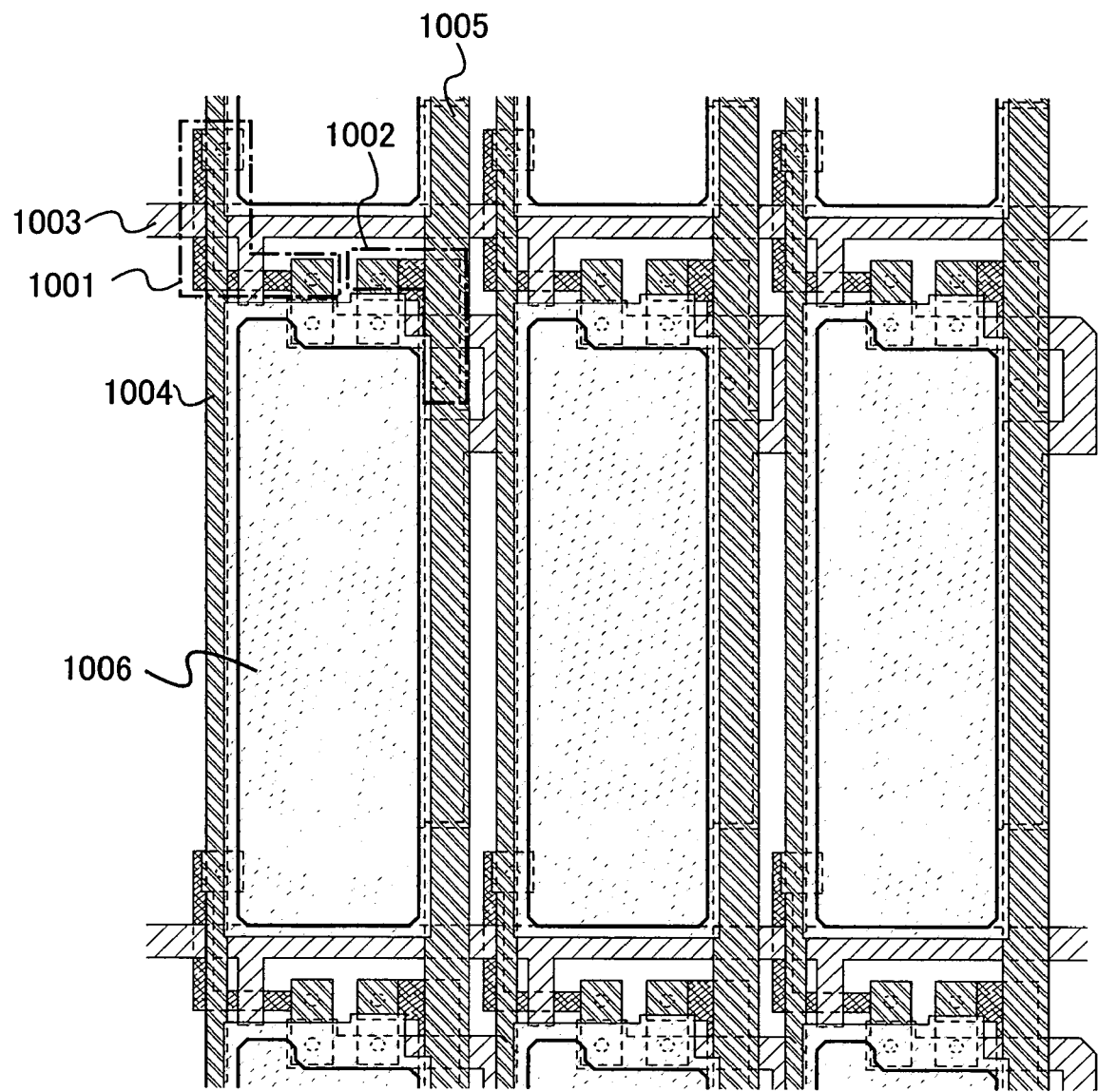
FIG. 7 is a top view of a light emitting device of the present invention.

Arrangement of a transistor, a light emitting element, and the like in the pixel portion is not particularly restricted. For example, arrangement shown in a top view of FIG. 7 can be employed. In FIG. 7, a first transistor 1001 has a first electrode connected to a source signal line 1004 and a second electrode connected to a gate electrode of a second transistor 1002. In addition, the second transistor has a first electrode connected to a current supply line 1005 and a second electrode connected to an electrode 1006 of a light emitting element. A part of a gate signal line 1003 functions as a gate electrode of the first transistor 1001.

Figure 8:
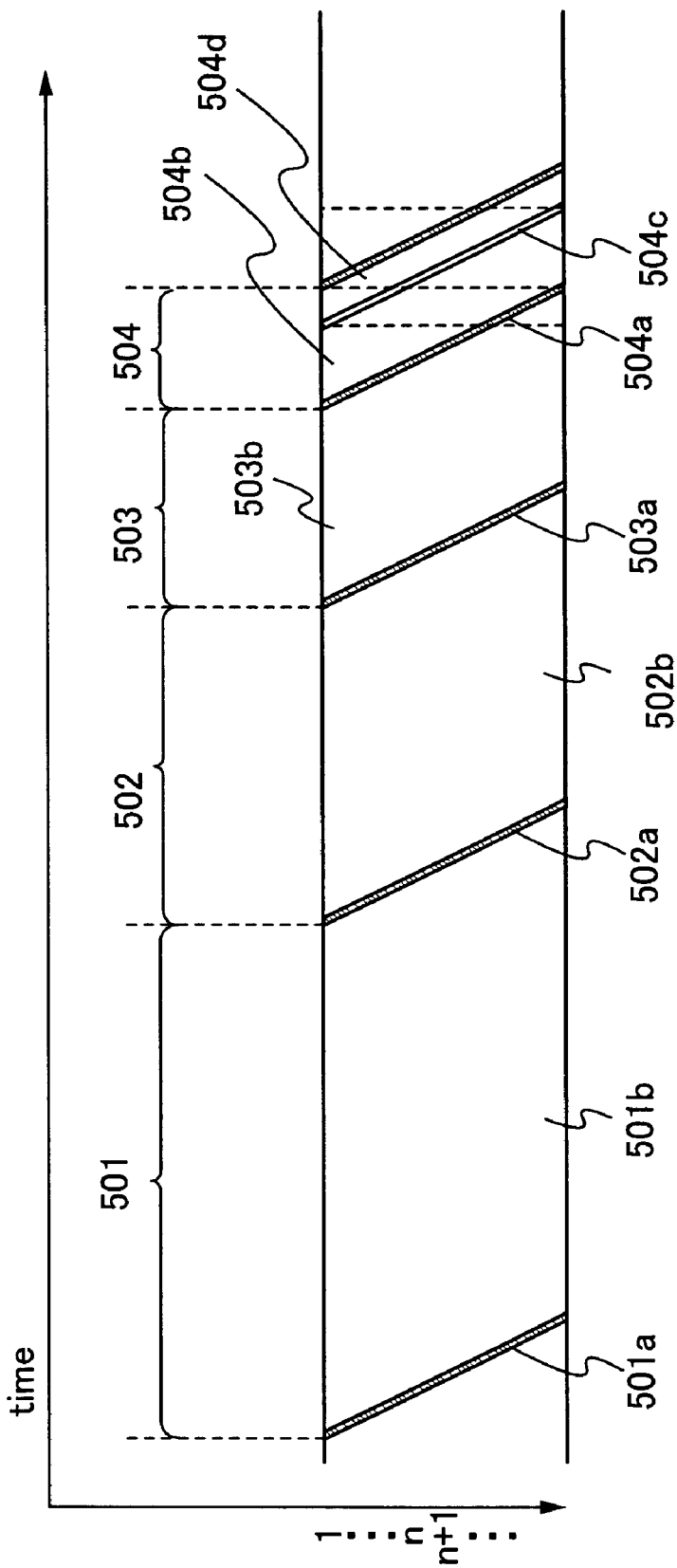
FIG. 8 is an explanatory view of an operation per frame of the present invention.

Next, a driving method is explained. FIG. 8 is a diagram explaining operation of a frame with time. In FIG. 8, the horizontal direction indicates passage of time, and the vertical direction indicates the number of scanning stages of a gate signal line of gate signal lines.

When a light emitting device of the present invention is used to display images, a rewrite operation and a display operation for a screen are repeated in a display period. Although the number of rewrites is not particularly restricted, at least approximately 60 times per second is preferable so as not to make a viewer recognize flickers (flicker). Here, a period in which a rewrite operation and a display operation are performed for a screen (one frame) is referred to as one frame period.

As shown in FIG. 8, one frame is time divided into four sub-frames 501, 502, 503, and 504 respectively including writing periods 501a, 502a, 503a, and 504a and retention periods 501b, 502b, 503b, and 504b. In the retention period, a light emitting element to which a signal for emitting light is applied is made to be in a light emitting state. The ratio of the length of the retention period of each sub-frame is the first sub-frame 501:the second sub-frame 502:the third sub-frame 503:the fourth sub-frame $504=2^3:2^2:2^1:2^0=8:4:2:1$, which makes 4-bit gradation display possible. However, the number of bits and the number of gradations are not restricted thereto. For example, eight sub-frames maybe provided so as to perform 8-bit gradation.

Operation in one frame is explained. First, in the sub-frame 501, writing operation is sequentially performed for each of the first row to the last row. Accordingly, the start time of the writing period is different depending on the row. A row in which the writing period 501a is completed, is sequentially moved into the retention period 501b. In the retention period, a light emitting element to which a signal for emitting light is applied is made to be in a light emitting state. In addition, the row in which the retention period 501b is completed, is sequentially moved into the next sub-frame 502, and a writing operation is sequentially performed for each of the first row to the last row as in the case of the sub-frame 501. The foregoing operation is repeated to complete the retention period 504b of the sub-frame 504. When the operation in the sub-frame 504 is completed, the row is moved into the next frame. Thus, the total of time for which light is emitted in each sub-frame is light emission time for each light emitting element in one frame. By varying this light emission time with respect to each light emitting element to have various combinations in one pixel, various colors with different brightness and chromaticity can be made.

As in the case of the sub-frame 504, when forcible termination of a retention period of a row in which writing is completed and which is moved into the retention period is required before writing in the last row is completed, an erasing period 504c is preferably provided after the retention period 504b and the row is controlled so as to be in a non-light-emitting state forcibly. In addition, the row made to be in the non-light-emitting state forcibly is kept in the non-light-emitting state for a certain period (this period is referred to as a non-light-emitting period 504d). Then, immediately after the writing period of the last row is completed, the rows are sequentially moved into the writing period of the next (or the frame), sequentially from the first row. This makes it possible to prevent the writing period of the sub-frame 504 from overlapping with the writing period of the next sub-frame.

Although the sub-frames 501 to 504 are arranged in the order of retention period from longest to shortest in this mode, the arrangement in the order as in this example is not always necessary. For example, the sub-frames 501 to 504 may be arranged in the order of retention period from the shortest to longest, or may be arranged in random order. In addition, the sub-frames may be divided further into a plurality of frames. In other words, scanning of the gate signal lines may be performed more than once while applying the same image signal.

Now, an operation of the circuit shown in FIG. 6 in a writing period and an erasing period is explained.

First, an operation in a writing period is explained. In the writing period, the the gate signal line 911 in an n-th row (n is a natural number) is electrically connected to the writing gate signal line driver circuit 913 through the switch 918, and disconnected to the erasing gate signal line driver circuit 914. In addition, the source signal line 912 is electrically connected to the source signal line driver circuit 915 through the switch 920. A signal is input to the gate electrode of the first transistor 901 connected to the gate signal line 911 in an n-th row (n is a natural number) to turn on the first transistor 901. At the same time, image signals are input simultaneously to the source signal lines in the first to last columns. It is to be noted that the image signals input from the respective source signal lines 912 are independent from each other. The image signal input from each of the source signal lines 912 is input to the gate electrode of the second transistor 902 through the first transistor 901 respectively connected to the source signal line. At the same time, whether the current supply line 917 is electrically connected to the light emitting element 903 or not is determined depending on the signal input to the second transistor 902 from the current supply line 917, so that whether the light emitting element 903 emits light or not is determined. For example, when the second transistor 902 is a p-channel transistor, the light emitting element 903 emits light with a Low Level signal input to the gate electrode of the second transistor 902. On the other hand, when the second transistor 902 is an n-channel transistor, the light emitting element 903 emits light with a High Level signal input to the gate electrode of the second transistor 902.

Next, an operation in an erasing period is explained. In the erasing period, the gate signal line 911 in an n-th row (n is a natural number) is electrically connected to the erasing gate signal line driver circuit 914 through the switch 919 and disconnected to the wiring gate signal line driver circuit 913.

In addition, the source signal line 912 is electrically connected to the power source 916 through the switch 920. A signal is input to the gate of the first transistor 901 connected to the gate signal line 911 in an n-throw to turn on the first transistor 901. At the same time, erasing signals are input simultaneously to the source signal lines in the first to last columns. The erasing signal input from the source signal line 912 is input to the gate electrode of the second transistor 902 through the first transistor 901 respectively connected to each of the source signal lines. The current supply line 917 and the light emitting element 903 are electrically disconnected due to the signal input to the second transistor 902. Then, the light emitting element 903 is forcibly made to be in a non-light-emitting state. For example, when the second transistor 902 is a p-channel transistor, the light emitting element 903 does not emit light with a High Level signal input to the gate electrode of the second transistor 902. On the other hand, when the second transistor 902 is an n-channel transistor, the light emitting element 903 does not emit light with a Low Level signal input to the gate electrode of the second transistor 902.

It is to be noted that, as for the n-th row (n is a natural number), signals for erasing are input by the operation described above in an erasing period. However, as described above, another row (referred to as an m-th row (m is a natural number)) may be in a writing period while the n-th row is in an erasing period. In such a case, it is necessary to input a signal for erasing to the n-th row and input a signal for writing to the m-th row by using a source signal line in the common column. Therefore, an operation explained below is preferable.

Immediately after the light emitting element 903 in the n-th row is in a non-light-emitting state by the foregoing operation in the erasing period, the gate signal line and the erasing gate signal line driver circuit 914 are made to be disconnected to each other and the switch 918 is switched to connect the source signal line and the source signal line driver circuit 915. Then, the source signal line is connected to the source signal line driver circuit 915 and the gate signal line is connected to the writing gate signal line driver circuit 913. Then, a signal is input selectively to the signal line in the m-th row from the writing gate signal line driver circuit 913 to turn on the first transistor and a signal for writing is input to the source signal lines in the first to last columns from the source signal line driver circuit 915. This signal makes the light emitting element in the m-th row emit light or not.

Immediately after the writing period of the m-th row is completed as described above, an erasing period of the (n+1)th row is started. For that purpose, the gate signal line and the writing gate signal line driver circuit 913 are disconnected to each other, and the switch 920 is switched to connect the source signal line and the power source 916. Further, the gate signal line is disconnected to the writing gate signal line driver circuit 913 and is connected to the erasing gate signal line driver circuit 914. Then, a signal is input selectively to the gate signal line in the (n+1)th row from the erasing gate signal line driver circuit 914 to turn on the first transistor, and at the same time an erasing signal is input from the power source 916. Thus, immediately after the erasing period of the (n+1)th row is completed, a writing period of the m-th row is started. Then, an erasing period and a writing period may be repeated in the same way until an erasing period of the last row is completed.

It is to be noted that although the writing period of the m-th row is provided between the erasing period of the n-th row and the erasing period of the (n+1)th row in this mode, it is not limited thereto. The writing period of the m-th row may be provided between the erasing period of the (n−1)th row and the erasing period of the n-th row.

In addition, in this mode, when the non-light-emitting period 504d is provided like in the sub-frame 504, the operation in which the erasing gate signal line driver circuit 914 and one gate signal line are disconnected to each other and the writing gate signal line driver circuit 913 and another gate signal line are connected to each other is repeated. Such operation may be performed in a frame in which a non-light-emitting period is not particularly provided.

Embodiment Mode 7

A mode of a cross-sectional view of a light emitting device having a light emitting element of the present invention is described with reference to FIGS. 9A to 9C.

Figure 9A:
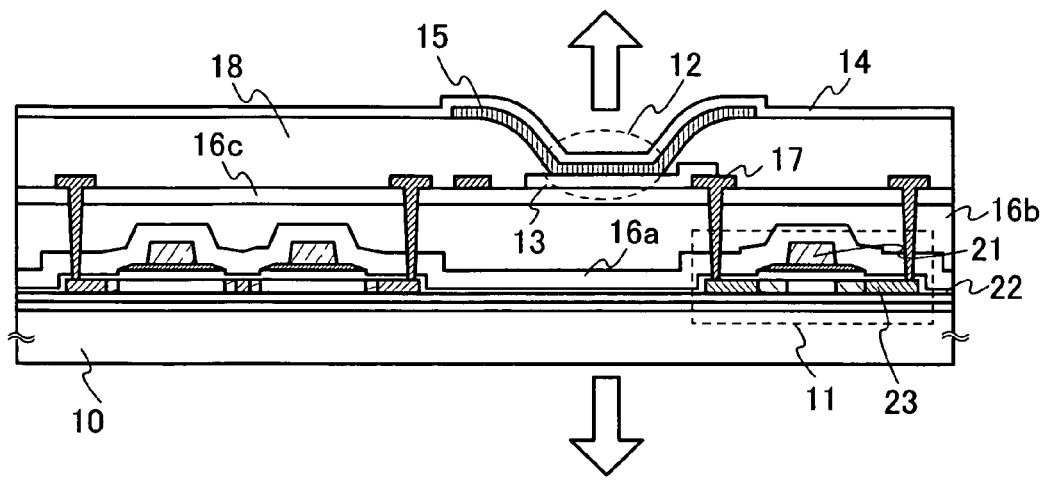
FIGS. 9A to 9C are cross-sectional views of a light emitting device of the present invention.
Figure 9B:
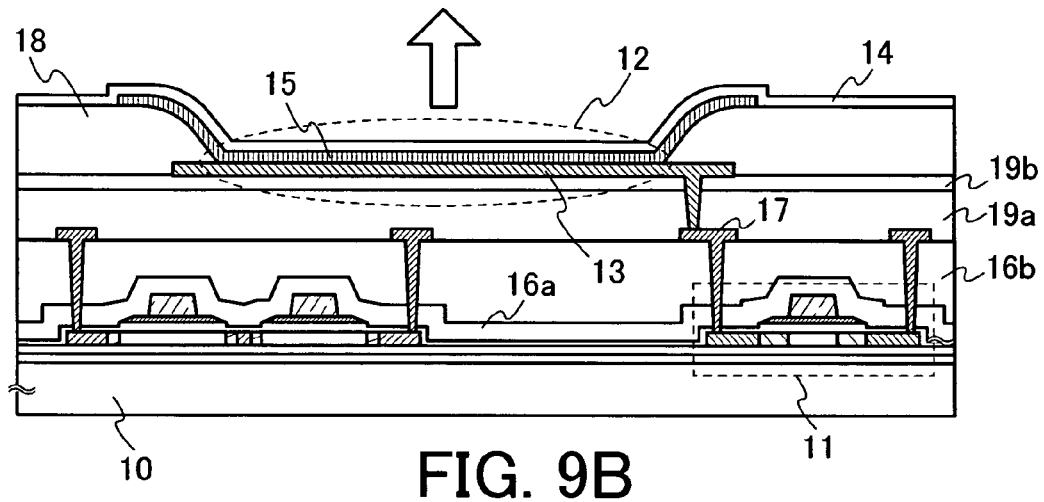
Figure 9C:
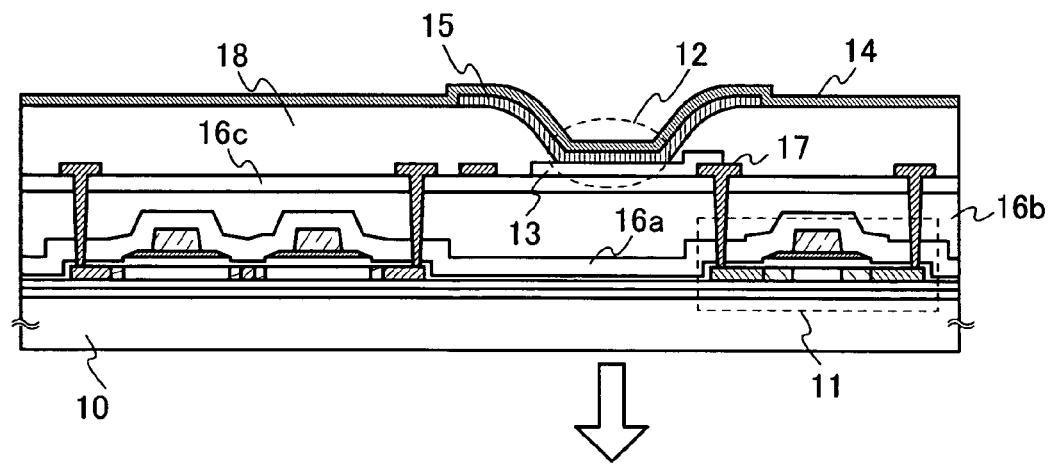

In each of FIGS. 9A to 9C, a rectangular portion surrounded by a dotted line is a transistor 11 provided for driving a light emitting element 12 of the present invention. The light emitting element 12 is a light emitting element of the present invention which has a layer 15, in which a layer for generating holes, a layer for generating electrons, and a layer containing a luminescent substance are stacked, between a first electrode 13 and a second electrode 14. A drain region of the transistor 11 and the first electrode 13 are electrically connected to each other by a wiring 17 running through first interlayer insulating films 16a, 16b, and 16c. In addition, the light emitting element 12 is separated by a partition wall layer 18 from another light emitting element provided adjacently. A light emitting device of the present invention having such a structure is provided over a substrate 10 in this mode.

It is to be noted that the transistor 11 shown in FIGS. 9A to 9C is a top-gate TFT in which a gate electrode is provided over a substrate with a semiconductor layer therebetween. However, the structure of the transistor 11 is not particularly restricted. For example, a bottom-gate TFT may be used. In the case of a bottom-gate TFT, a TFT in which a protective film is formed over a semiconductor layer which forms a channel (a channel-protected TFT) may be employed, or a TFT in which a part of a semiconductor layer which forms a channel is concave (a channel-etched TFT) may be employed. It is to be noted that 21 is a gate electrode, 22 is a gate insulating film, and 23 is a semiconductor layer.

In addition, a semiconductor layer for forming the transistor 11 may be either crystalline or noncrystalline, or alternatively, may be semi-amorphous or the like.

The following describes a semi-amorphous semiconductor. The semi-amorphous semiconductor is a semiconductor which has an intermediate structure between amorphous and crystalline (such as single crystalline or polycrystalline) structures and has a third state that is stable in terms of free energy and which includes a crystalline region that has a short range order and lattice distortion. Further, a crystal grain of 0.5 to 20 nm is included in at least a region in a film of the semi-amorphous semiconductor. Raman spectrum derived from L-O phonon is shifted to a lower wavenumber side than 520 cm$^{-1}$. Diffraction peaks of (111) and (220) which are said to be derived from a silicon crystal lattice are observed in the semi-amorphous semiconductor by X-ray diffraction. The semi-amorphous semiconductor contains hydrogen or halogen of 1 atomic % or more for terminating dangling bonds (dangling bonds). A semi-amorphous semiconductor is also referred to as a microcrystalline semiconductor (microcrystalline semiconductor) and formed by glow discharge decomposition (plasma CVD) of silicon source gas. As silicon source gas, in addition to $SiH_4$; $Si_2H_6$, $SiH_2Cl_2$, $SiHCl_3$, $SiCl_4$, $SiF_4$, or the like can be used. Each of these silicon source gases may also be diluted with $H_2$, or a mixture of $H_2$ and one or more of rare gas elements selected from He, Ar, Kr, and Ne. The dilution rate is set to be in the range of 1:2 to 1:1,000. The pressure is set to be approximately in the range of 0.1 Pa to 133 Pa. The power frequency is set to be 1 MHz to 120 MHz, preferably, 13 MHz to 60 MHz. The substrate heating temperature may be set to be 300° C. or less, preferably, 100 to 250° C. As for impurity elements contained in the film, concentration of impurities of atmospheric constituents such as oxygen, nitrogen, and carbon is preferably set to be $1 \times 10^{20}$ atoms/cm$^3$ or less. In particular, the oxygen concentration is set to be $5 \times 10^{19}$ atoms/cm$^3$ or less, preferably, $1 \times 10^{19}$ atoms/cm$^3$ or less. It is to be noted that when a semi-amorphous semiconductor is used for a TFT (thin film transistor), the mobility thereof is 1 to 10 cm$^2$/Vsec.

In addition, as specific examples of crystalline semiconductors for the semiconductor layer, single crystal or polycrystalline silicon and silicon-germanium, or the like can be given. They may be formed by laser crystallization or may be formed by crystallization with a solid-phase growth method using nickel or the like.

In the case of using an amorphous substance, for example, amorphous silicon to form the semiconductor layer, all of the transistor 11 and another transistors (transistors forming the circuit for driving the light emitting element) included in the first circuit in the light emitting devices are preferably n-channel transistors. Other than that case, the light emitting device may have a circuit including one of n-channel transistors and p-channel transistors or may have a circuit including both n-channel transistors and p-channel transistors.

Further, the first interlayer insulating films 16a to 16c may be a multilayer as shown in FIGS. 9A to 9C or may be a single layer. It is to be noted that the 16a is formed from an inorganic substance such as silicon oxide or silicon nitride and 16b is formed from a substance with self-flatness such as acrylic, siloxane (which has a skeletal structure formed by the bond of silicon (Si) and oxygen (O), in which at least hydrogen is used as a substituent), and silicon oxide which can be deposited by being applied. The 16c is formed of a film containing silicon nitride film having argon (Ar). It is to be noted that the substances for forming the respective layers are not particularly restricted; therefore, a substance other than the substances mentioned above may be used. Moreover, a layer containing a substance other than these substances may be combined. In this way, the first interlayer insulting films 16a to 16c may be formed from both an inorganic substance and an organic substance, or either of an inorganic film and an organic film.

As for the partition wall layer 18, an edge portion preferably has a shape varying continuously in curvature radius. In addition, a substance such as acrylic, siloxane, resist, or silicon oxide is used to form the partition wall layer 18. It is to be noted that either or both an inorganic film and an organic film may be used for the partition wall layer 18.

In FIGS. 9A and 9C, only the first interlayer insulating films 16a to 16c are provided between the transistor 11 and the light emitting element 12. However, as shown in FIG. 9B, second interlayer insulating films 19a and 19b may be provided in addition to the first interlayer insulating films 16a and 16b. In the light emitting device shown in FIG. 9B, the first electrode 13 is connected to the wiring 17 through the second interlayer insulating films 19a and 19b.

The second interlayer insulating films 19a and 19b may be a multilayer or a single layer as in the case of the first interlayer insulating films 16a to 16c. The 19a is formed from a substance with self-flatness such as acrylic, siloxane (which has a skeletal structure formed by a silicon (Si)-oxygen (O) bond, in which at least hydrogen is used as a substituent) or silicon oxide which can be formed by being applied. In addition, the 19b is formed of a silicon nitride film having argon (Ar). It is to be noted that the substances contained in the respective layers are not particularly restricted; therefore, a substance other than the substances mentioned above may be used. In addition, a layer containing a substance other than these substances may be combined. In this way, both an inorganic substance and an organic substance or one of an inorganic substance and an organic substance may be used to form the second interlayer insulating films 19a and 19b.

In the light emitting element 12, in the case where both the first electrode and the second electrode are formed by using a light transmitting substance, emitted light can be extracted from both the first electrode 13 side and the second electrode 14 side as indicated by outline arrows in FIG. 9A. In the case where only the second electrode 14 is formed from a light transmitting substance, emitted light can be extracted from only the second electrode 14 side as indicated by an outline arrow in FIG. 9B. In this case, the first electrode 13 preferably contains a highly reflective material or a film formed from a highly reflective material (a reflective film) is preferably provided below the first electrode 13. In the case where only the first electrode 13 is formed from a light transmitting substance, emitted light can be extracted from only the first electrode 13 side as indicated by an outline arrow in FIG. 9C. In this case, the second electrode 14 preferably has a highly reflective material or a reflective film is preferably provided above the second electrode 14.

In addition, in the light emitting element 12, the layer 15 may be stacked layers so that the light emitting element 12 operates when a voltage is applied so that the potential of the second electrode 14 is higher than the potential of the first electrode 13. Alternatively, the layer 15 may be stacked layers so that the light emitting element 12 operates when a voltage is applied so that the potential of the second electrode 14 is lower than the potential of the first electrode 13. The transistor 11 is an n-channel transistor in the former case, and the transistor 11 is a p-channel transistor in the latter case.

Although an active light emitting device in which driving of a light emitting element is controlled by a transistor is explained in this embodiment mode, a passive light emitting device in which a light emitting element is driven without an element for driving such as a transistor may be used. A passive light emitting device can also be driven with low power consumption by including a light emitting element of the present invention which is operated with low drive voltage.

Embodiment Mode 8

A light emitting device including the light emitting element of the present invention can display a preferable image. Therefore, electronic equipments that are capable of providing an excellent image can be obtained by applying the light emitting device of the present invention to a display portion of the electronic equipments. In addition, the light emitting device including the light emitting element of the present invention can be driven with low power consumption because it has preferable luminous efficiency. Therefore, electronic equipments with low power consumption can be obtained by applying the light emitting device of the present invention to the display portion of the electronic devices, and for example, a telephone set that has long battery standing time, and the like can be obtained.

Figure 10A:
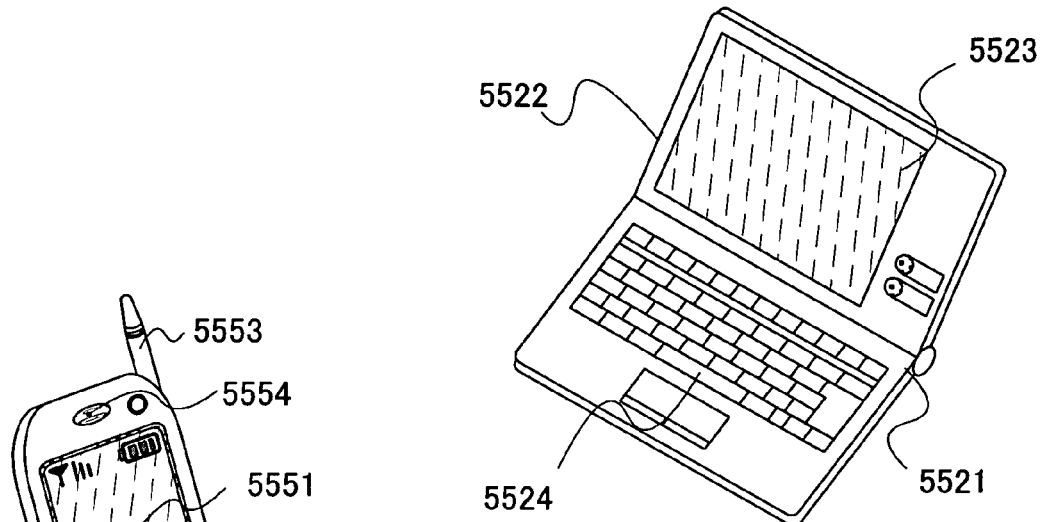
FIGS. 10A to 10C are views showing electronic equipments of the present invention.
Figure 10B:
Figure 10C:
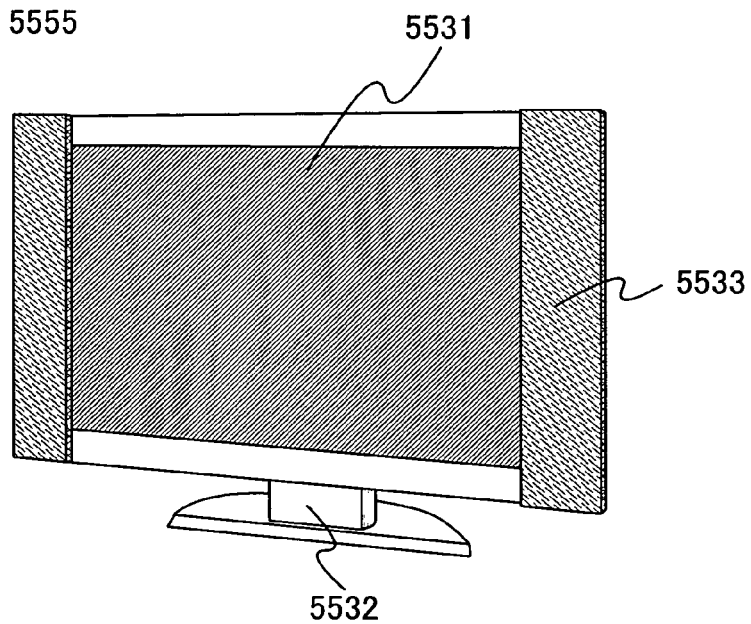

Examples of electronic equipments mounted with the light emitting devices to which the present invention is applied are shown in FIGS. 10A to 10C.

FIG. 10A is a laptop personal computer manufactured by applying the present invention, which includes a main body 5521, a frame body 5522, a display portion 5523, a keyboard 5524, and the like. The personal computer can be completed by incorporating the light emitting device including the light emitting element of the present invention thereinto as a display portion.

FIG. 10B is a telephone set manufactured by applying the present invention, in which a main body 5552 includes a display portion 5551, an audio output portion 5554, an audio input portion 5555, operation switches 5556 and 5557, an antenna 5553, and the like. The telephone set can be completed by incorporating the light emitting device including the light emitting element of the present invention thereinto as a display portion.

FIG. 10C is a television set manufactured by applying the present invention, which includes a display portion 5531, a frame body 5532, a speaker 5533, and the like. The television set can be completed by incorporating the light emitting device including the light emitting element of the present invention thereinto as a display portion.

As described above, the light emitting devices of the present invention are extremely suitable to be used as the display portion of various kinds of electronic equipment.

Although the personal computer and the like are described in the present embodiment, besides, the light emitting device including the light emitting element of the present invention may also be mounted on a navigation system, a lighting apparatus, or the like.

Embodiment 1

In the present embodiment, a method for synthesizing 2,3-bis(4-trifluoromethylphenyl)quinoxaline (abbreviation: CF$_3$DPQ) Represented by a Structural Formula (19) is explained.

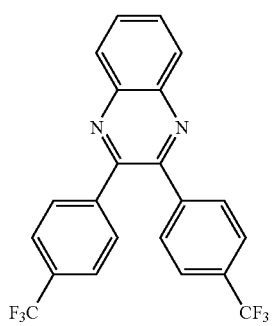

(19)

[Step 1: Synthesis of intermediate a]

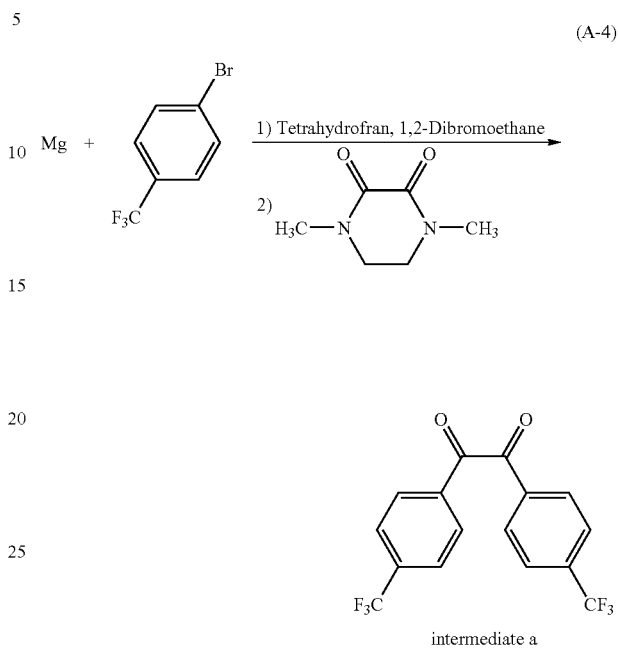

intermediate a

In accordance with the above scheme (A-4), 2.67 g of magnesium was suspended in 3 ml of THF (Tetrahydrofran), and a small amount of 1,2-dibromoethane was added. A solution in which 110 ml of THF was added to 25.00 g of 4-bromobenzotrifluorido, was dropped, and the solution was stirred for 2 hours under heat and reflux. 7.82 g of 1,4-dimethylpiperazine-2,3-dione was added to the solution cooled to a room temperature, and the solution was stirred for 6 hours under heat and reflux. 200 ml of 10% hydrochloric acid was added to the solution cooled to a room temperature, and an organic layer was extracted with chloroform. After drying with sodium sulfate, a solvent was condensed. Purification was performed by column chromatography (hexane/dichloromethane base) to obtain an intermediate a (yellow powder, yield: 30%).

[Step 2: Synthesis of ligand 2,3-bis(4-trifluoromethylphenyl) quinoxaline (abbreviation: CF$_3$DPQ) of the Present Invention]

-continued

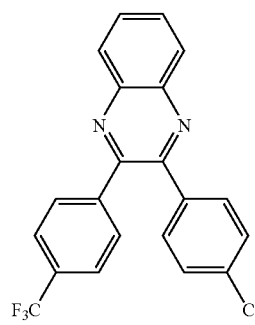

In accordance with the above scheme (A-5), 100 ml of chloroform was added to 2.36 g of the obtained intermediate a and 0.74 g of 1,2-phenylenediamine, and the solution was stirred for 8 hours under heat and reflux. The solution cooled to a room temperature was washed with 10% hydrochloric acid and then with a saturated sodium chloride solution, and dried with sodium sulfate. Then, the solvent was condensed to obtain a ligand 2,3-bis(4-trifluoromethylphenyl)quinoxaline (abbreviation: CF$_3$DPQ) of the present invention (pale yellow powder, yield: 91%).

Embodiment 2

In the present embodiment, a method for synthesizing an organometallic complex (acetylacetonato)bis[2,3-bis(4-trifluoromethylphenyl) quinoxalinato-N,C$^{2'}$]iridium(III) (abbreviation: [Ir(CF$_3$dpq)$_2$(acac)]) of the present invention represented by a structural formula (11) with the use of CF$_3$DPQ synthesized in Embodiment 1 is explained.

(11)

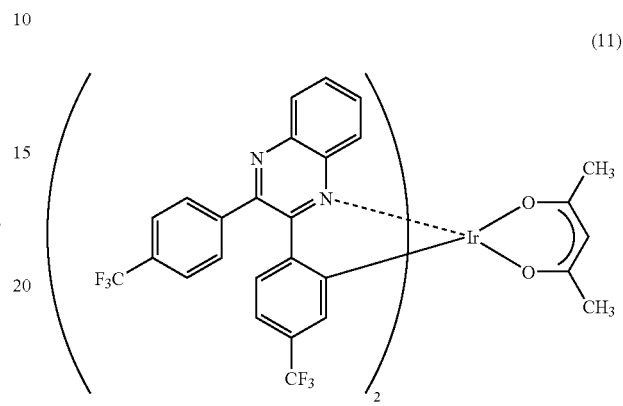

[Step 1: Synthesis of Dinuclear Complex (abbreviation: [Ir(CF$_3$dpq)$_2$Cl]$_2$)]

(A-6)

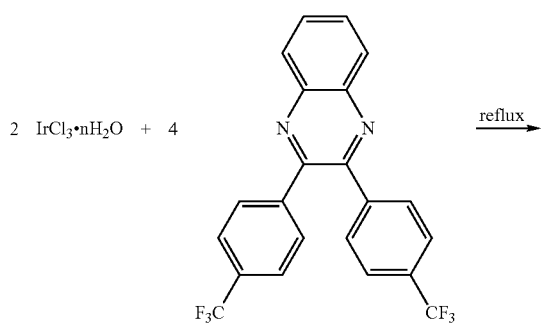 $\xrightarrow{\text{reflux}}$

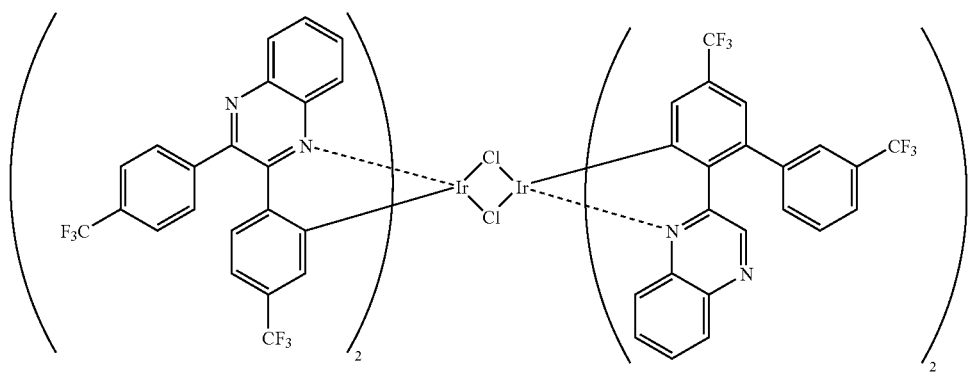

In accordance with the above scheme (A-6), first, with a mixture of 30 ml of 2-ethoxyethanol and 10 ml of water as a solvent, 2.59 g of the ligand CF$_3$DPQ and 0.74 g of iridium chloride hydrochloride-hydrate (IrCl$_3$nH$_2$O) were mixed, and held at reflux in a nitrogen atmosphere for 15 hours to obtain a dinuclear complex [Ir(CF$_3$dpq)$_2$Cl]$_2$ (brown powder, yield: 48%).

[Step 2: Synthesis of Organometallic Compound (acetylacetonato)bis[2,3-bis(4-trifluoromethylphenyl) quinoxalinato-N,C$^{2'}$]iridium(III) (abbreviation: [Ir(CF$_3$dpq)$_2$(acac)]) of the present invention]

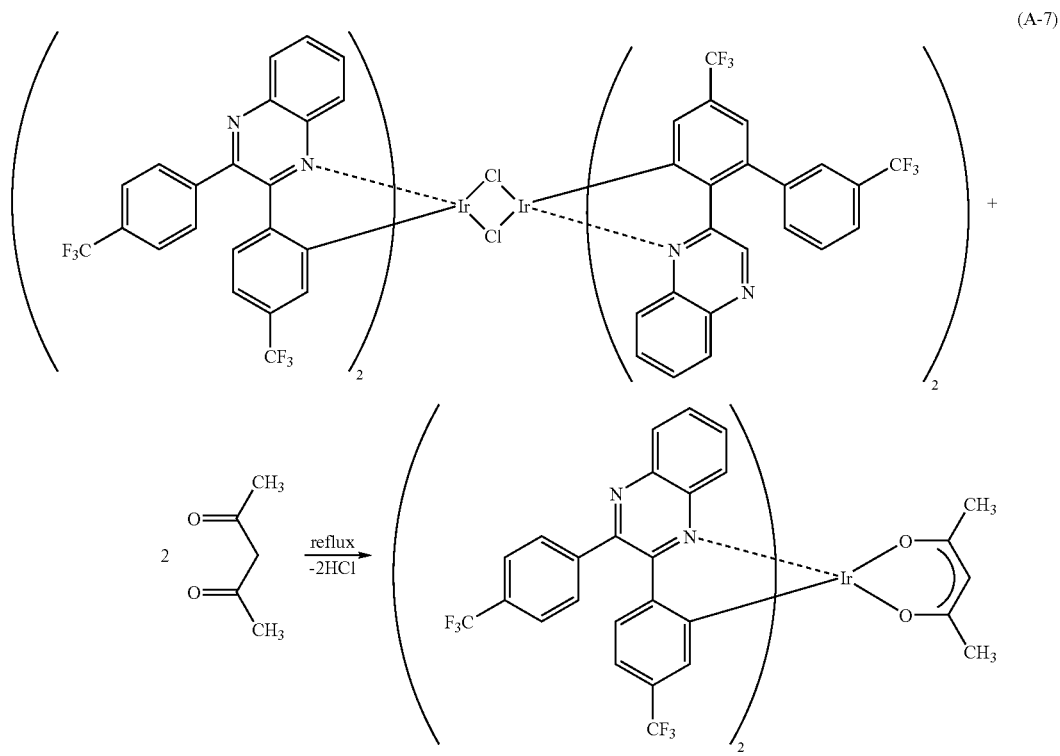

(A-7)

In accordance with the above scheme (A-7), with 15 ml of 2-ethoxyethanol as a solvent, 1.24 g of the above obtained [Ir(CF$_3$dpq)$_2$Cl]$_2$, 0.18 ml of acetylacetone (Hacac), and 0.61 g of sodium carbonate were mixed, and held at reflux in a nitrogen atmosphere for 16 hours to obtain an organometallic compound (acetylacetonato)bis[2,3-bis(4-trifluoromethylphenyl)quinoxalinato-N,C$^{2'}$]iridium(III) (abbreviation: [Ir(CF$_3$dpq)$_2$(acac)]) of the present invention (dark red powder, yield: 3%). The data of NMR is shown below.

$^1$H-NMR. δ(CDCl$_3$): 8.17(m,8H), 7.95(brm,4H), 7.76(td, 2H), 7.56(td,2H), 7.17(d,2H), 6.94(dd,2H), 6.67(s,2H), 5.30 (s,1H), 1.63(s,6H).

Figure 11:
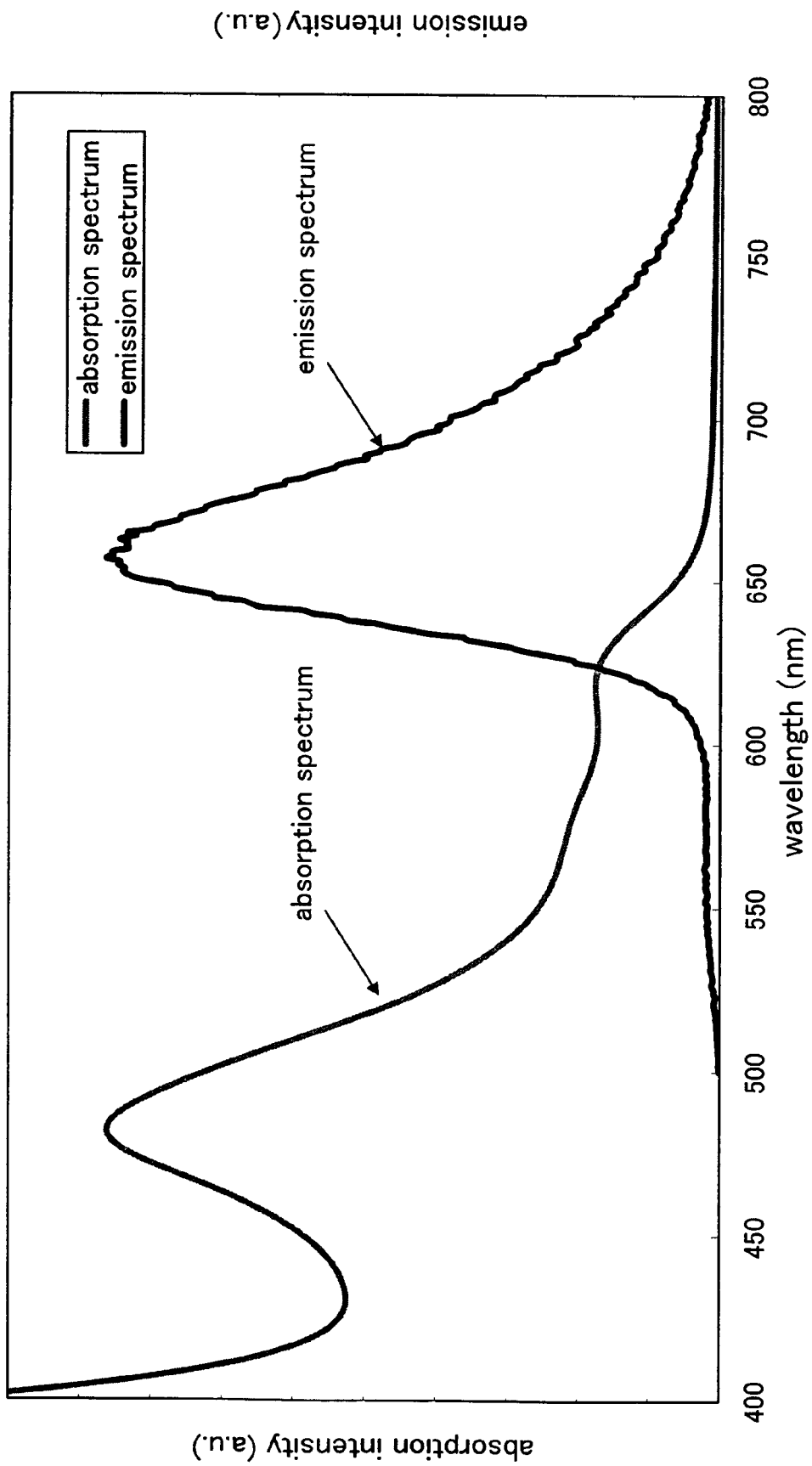
FIG. 11 is a graph showing an absorption spectrum and an emission spectrum of an organometallic complex of the present invention.

FIG. 11 shows an absorption spectrum and an emission spectrum of the obtained Ir(CF$_3$dpq)$_2$(acac) in dichloromethane. In FIG. 11, the horizontal axis indicates a wavelength (nm), and the vertical axis indicates intensity (arbitrary unit). The organometallic compound Ir(CF$_3$dpq)$_2$(acac) of the present invention has absorption peaks at 370 nm, 482 nm, 570 nm (shoulder), and 620 nm. In addition, the emission spectrum showed an emission peak at 665 nm and red emission of light. Further, a half width of the emission spectrum is comparatively narrow, and a sharp peak and light emission with favorable color purity are represented.

As for the obtained Ir(CF$_3$dpq)$_2$(acac), the several absorption peaks are observed on the longer wavelength side. This is a unique absorption to an organometallic complex, which is often observed in an orthometalated complex or the like, and is considered to correspond to singlet MLCT (Metal to ligand charge transfer) transition, triplet π-π* transition, triplet MLCT transition, or the like. In particular, the absorption peak on the longest wavelength side spreads toward the bottom broadly in the visible region, which is believed to be a unique absorption spectrum to a triplet MLCT transition. In other words, it was determined that Ir(CF$_3$dpq)$_2$(acac) is a compound capable of direct photo-excitation to a triplet excited state and intersystem crossing.

Further, a gas containing oxygen was injected into a dichloromethane solution including the obtained Ir(CF$_3$dpq)$_2$ (acac), and the emission intensity was examined when the Ir(CF$_3$dpq)$_2$(acac) with dissolved oxygen was made to emit light. Furthermore, argon was injected into a dichloromethane solution including the obtained Ir(CF$_3$dpq)$_2$ (acac), and the emission intensity was examined when the Ir(CF$_3$dpq)$_2$(acac) with dissolved argon was made to emit light. From the result, it was determined that luminescence derived from Ir(CF$_3$dpq)$_2$(acac) shows the same tendency as luminescence of a phosphorescent substance, where the emission intensity in the state with dissolved argon is stronger than the emission intensity in the state with dissolved oxygen. Accordingly, luminescence derived from Ir(CF$_3$dpq)$_2$(acac) is believed to be phosphorescence.

The Ir(CF$_3$dpq)$_2$(acac) synthesized in the present embodiment has the strong absorption corresponding to the triplet MLCT transition and has the comparatively strong absorption in the entire visible region as shown in FIG. 11. Therefore, the organometallic complex of the present invention is used for a device utilizing absorption of visible light, for example used as a dye of a dye sensitized solar cell, so that a device with high conversion efficiency can be obtained.

Further, in the Ir(CF$_3$dpq)$_2$(acac) synthesized in the present embodiment, a difference between the peak of the triplet MLCT absorption (620 nm) and the peak of the emission spectrum (665 nm), in other words a Stokes shift is small. From this, it is suggested that a molecule in the excited state is stable. That is, the organometallic complex of the present invention is a preferable material for a photoelectronics device such as a dye sensitized solar cell and a light emitting element, because the molecule in the triplet MLCT excited state is stable.

Furthermore, since the Ir(CF$_3$dpq)$_2$(acac) synthesized in the present embodiment can be made in paste by mixing with a solvent, the Ir(CF$_3$dpq)$_2$(acac) can be coated in paste.

Embodiment 3

In the present embodiment, a method for synthesizing an organometallic compound bis[2,3-bis(4-trifluoromethylphenyl)quinoxalinato-N,C$^{2'}$](picolinato)iridium(III) (abbreviation: Ir(CF$_3$dpq)$_2$(pic)) of the present invention represented by the structural formula (13) is explained.

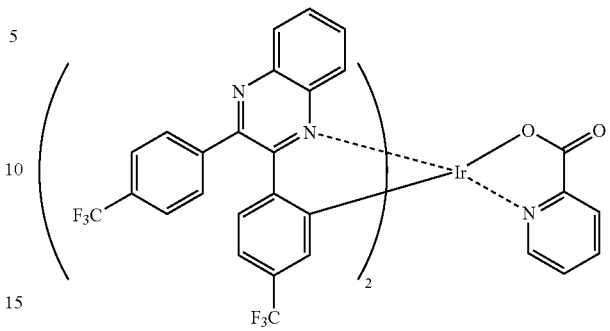

(13)

As a row material, the dinuclear complex ([Ir(CF$_3$dpq)$_2$Cl]$_2$) obtained by Step 1 in Embodiment 2 is used. First, with 30 ml of dichloromethane as a solvent, 1.77 g of [Ir(CF$_3$dpq)$_2$Cl]$_2$ and 0.82 g of picolinic acid (Hpic) were mixed, and held at reflux in a nitrogen atmosphere for 14 hours. Subsequently, the obtained reacted solution was condensed and exsiccated by an evaporator, and recrystallization was performed with a methanol solvent. The obtained powder was washed with methanol and then with hexane to obtain an organometallic compound Ir(cf$_3$dpq)$_2$(pic) of the present invention (brown powder, yield: 80%). A synthesis scheme of the present embodiment is shown below (A-8).

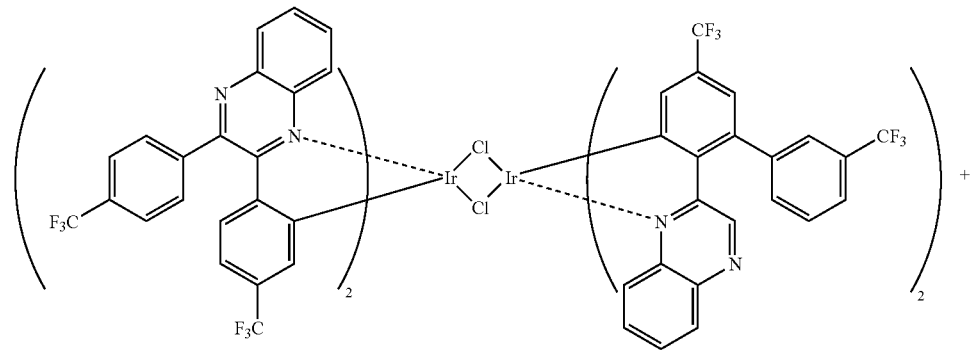

(A-8)

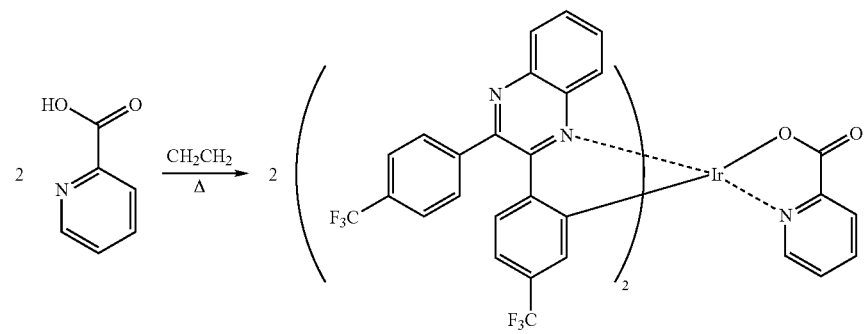

Further, the data of $^1$H-NMR of the obtained compound is shown below.

$^1$H-NMR. δ(CDCl$_3$):8.65(m,1H), 8.37(d,1H), 8.19(m, 3H), 8.08(m,1H), 7.90(m,4H), 7.83(m,1H), 7.76(m,1H), 7.62 (m,2H), 7.39(d,1H), 7.30(m,2H), 7.21(m,2H), 7.15(m,2H), 7.06(dd,1H), 6.99(s,1H), 6.93(m,1H), 6.34(s,1H).

The decomposition temperature $T_d$ of the obtained organometallic compound Ir(CF$_3$dpq)$_2$(piC) of the present invention was measured by TG-DTA to find $T_d$=350° C., and thus, it was determined that the favorable heat resistance is shown.

Figure 12:
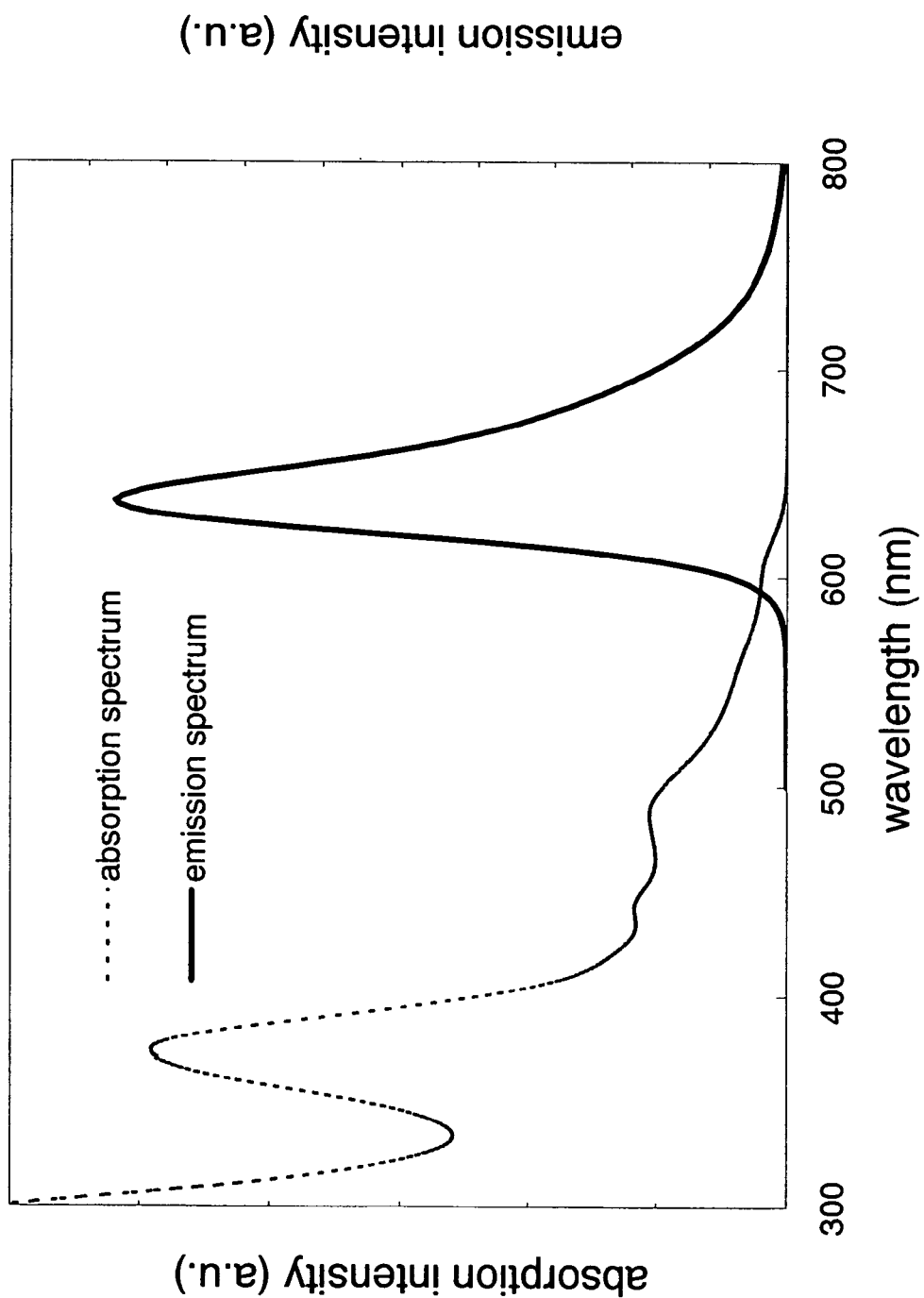
FIG. 12 is a graph showing a spectrum of a compound of the present invention.

Further, FIG. 12 shows an absorption spectrum and an emission spectrum of the obtained Ir(CF$_3$dpq)$_2$(pic) in dichloromethane at a room temperature. In FIG. 12, the horizontal axis indicates a wavelength (nm), and the vertical axis indicates absorbance (arbitrary unit) and emission intensity (arbitrary unit). The organometallic compound Ir(CF$_3$dpq)$_2$ (pic) of the present invention has absorption peaks at 374 nm, 441 nm, 486 nm, 553 nm (shoulder), and 606 nm. In addition, the emission spectrum showed an emission peak at 637 nm and red emission of light. Further, a half width of 50 nm the emission spectrum is extremely narrow, and a sharp spectrum and light emission with favorable color purity are represented.

In the obtained Ir(CF$_3$dpq)$_2$(pic), several absorption peaks are observed on the longer wavelength side. This is a unique absorption to an organometallic complex, which is often observed in an orthometalated complex or the like, and is considered to correspond to a singlet MLCT (Metal to ligand charge transfer) transition, triplet π-π* transition, triplet MLCT transition, or the like. In particular, the absorption peak on the longest wavelength side spreads toward a bottom broadly in the visible region, which is believed to be a unique absorption spectrum to triplet MLCT transition. In other words, it was determined that Ir(CF$_3$dpq)$_2$(pic) is a compound that is capable of direct photo-excitation to a triplet excited state and intersystem crossing.

Further, a gas containing oxygen was injected into a dichloromethane solution including the obtained Ir(CF$_3$dpq)$_2$(pic), and the emission intensity was examined when the Ir(CF$_3$dpq)$_2$(pic) with dissolved oxygen was made to emit light. Furthermore, argon was injected into a dichloromethane solution including the obtained Ir(CF$_3$dpq)$_2$(pic), and the emission intensity was examined when the Ir(CF$_3$dpq)$_2$(pic) with dissolved argon was made to emit light. From the result, it was determined that luminescence derived from Ir(CF$_3$dpq)$_2$(pic) shows the same tendency as a substance emitting phosphorescence, where the emission intensity in the state with dissolved argon is stronger than the emission intensity in the state with dissolved oxygen. Accordingly, luminescence derived from Ir(CF$_3$dpq)$_2$(pic) is believed to be phosphorescence.

The Ir(CF$_3$dpq)$_2$(pic) synthesized in the present embodiment has the strong absorption corresponding to the triplet MLCT transition and has the comparatively strong absorption in the entire visible region as shown in FIG. 12. Therefore, the organometallic complex of the present invention is used for a device utilizing absorption of visible light, for example used as a dye of a dye sensitized solar cell, so that a device having high conversion efficiency can be obtained.

Further, in the Ir(CF$_3$dpq)$_2$(pic) synthesized in the present embodiment, a difference between the peak of the triplet MLCT transition (606 nm) and the peak of the emission spectrum (637 nm), in other words, a Stokes shift, is small. From this, it is suggested that a molecule in the excited state is stable. That is, the organometallic complex of the present invention is a preferable material for a photoelectronics device such as a dye sensitized solar cell and a light emitting element, because the molecule in the triplet MLCT excited state is stable.

Embodiment 4

In the present embodiment, a light emitting element using the organometallic complex Ir(CF$_3$dpq)$_2$(pic) of the present invention, which is synthesized in Embodiment 3, as a luminescent substance will be specifically illustrated. It is to be noted that the reference numerals in FIG. 1 are cited for description in the present embodiment.

First, indium tin oxide containing silicon oxide was deposited by sputtering over a glass substrate to form a first electrode 151. The first electrode 151 was made to have a thickness of 110 nm and a size of 2 mm square.

Next, the glass substrate provided with the first electrode 151 was fixed to a holder that is provided in a vacuum evaporation apparatus so that the side where the first electrode 151 was formed faced downward.

After reducing pressure in the vacuum evaporation apparatus so as to be 1×10$^{-4}$ Pa, a hole injecting layer 161 was formed over the first electrode 151 by performing co-evaporation of α-NPD (4,4'-Bis[N-(1-naphthyl)-N-phenylamino] biphenyl) and molybdenum trioxide. The hole injecting layer 161 was made to have a thickness of 50 nm. It is to be noted that the ratio of NPB to the molybdenum trioxide was controlled to be 4:1 (=NPB:molybdenum trioxide) in mass ratio.

Next, NPB having a thickness of 10 nm was deposited over the hole injecting layer 161 to form a hole transporting layer 162.

In addition, a light emitting layer 163 containing CBP (4,4'-N,N'-dicarbazol-biphenyl) and Ir(CF$_3$dpq)$_2$(pic) was formed over the hole transporting layer 162 by a co-evaporation method. The light emitting layer 163 was set to have a thickness of 30 nm, and the mass ratio of CBP to Ir(CF$_3$dpq)$_2$ (pic) was set to be 1:0.025 (=CBP:Ir(CF$_3$dpq)$_2$(pic)). Accordingly, Ir(CF$_3$dpq)$_2$(pic) was in a state to be included in a layer in which CBP is a matrix (matrix). In this case, Ir(CF$_3$dpq)$_2$ (pic) is referred to as guest, and CBP is referred to as host.

Then, BCP (Bathocuproine; 2,9-Dimethyl-4,7-diphenyl-1, 10-phenanthroline) was deposited to have a thickness of 10 nm over the light emitting layer 163 to form an electron transporting layer 164. It is to be noted that, as in the present embodiment, an electron transporting layer may be particularly referred to as a hole blocking layer, which has ionization potential that is larger than that of a host, and has a function of preventing holes from passing through a layer serving as a light emitting layer (light emitting layer 163 in the present embodiment) to an electrode serving as a cathode (a second electrode 152 in the present embodiment).

In addition, an electron injecting layer 165 containing Alq$_3$ and Li was formed over the electron transporting layer 164 by a co-evaporation method. The electron injecting layer 165 was set to have a thickness of 50 nm. Further, the mass ratio of Alq$_3$ to Li was set to be 1:0.01 (=Alq$_3$:Li).

Finally, the second electrode 152 formed of aluminum was formed over the electron injecting layer 165. The second electrode 152 was made to have a thickness of 200 nm.

The light emitting element manufactured as described above emits light when current flows by applying voltage so that potential of the first electrode 151 is higher than that of the second electrode 152, excitation energy is generated in the light emitting layer 163 by recombining the electrons and the holes, and excited Ir(CF$_3$dpq)$_2$(pic) returns to the ground state.

Sealing operation was performed in a nitrogen atmosphere in a glove box so that this light emitting element was not exposed to the atmosphere. Then, operating characteristics of the light emitting element were measured. It is to be noted that the measurement was performed at a room temperature (the atmosphere kept at 25° C.).

Figure 13:
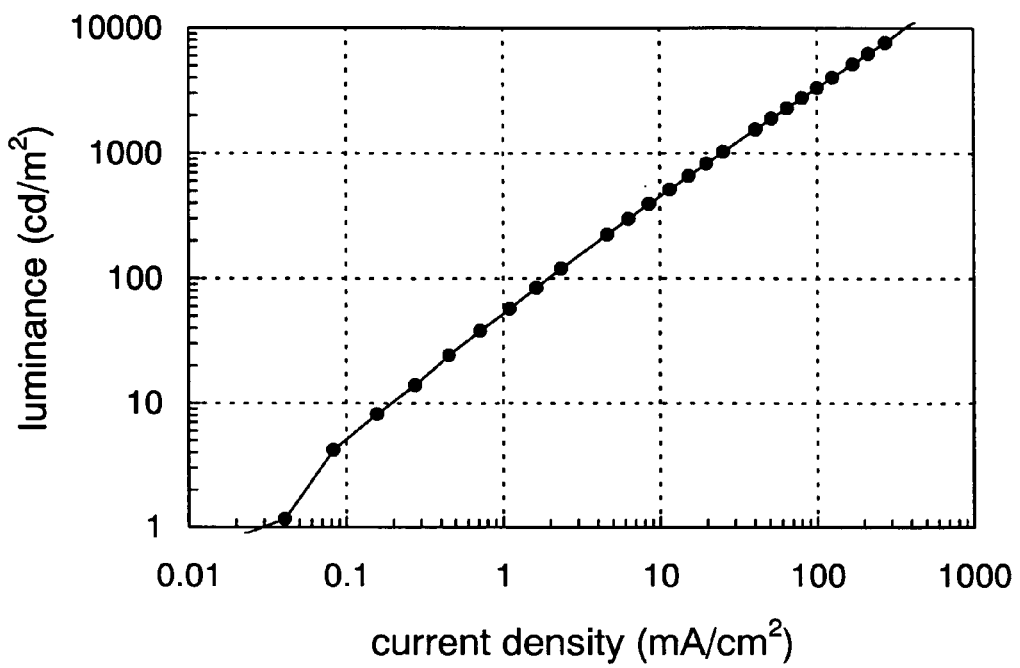
FIG. 13 is a graph showing current density-luminance characteristics of a light emitting element of the present invention.
Figure 14:
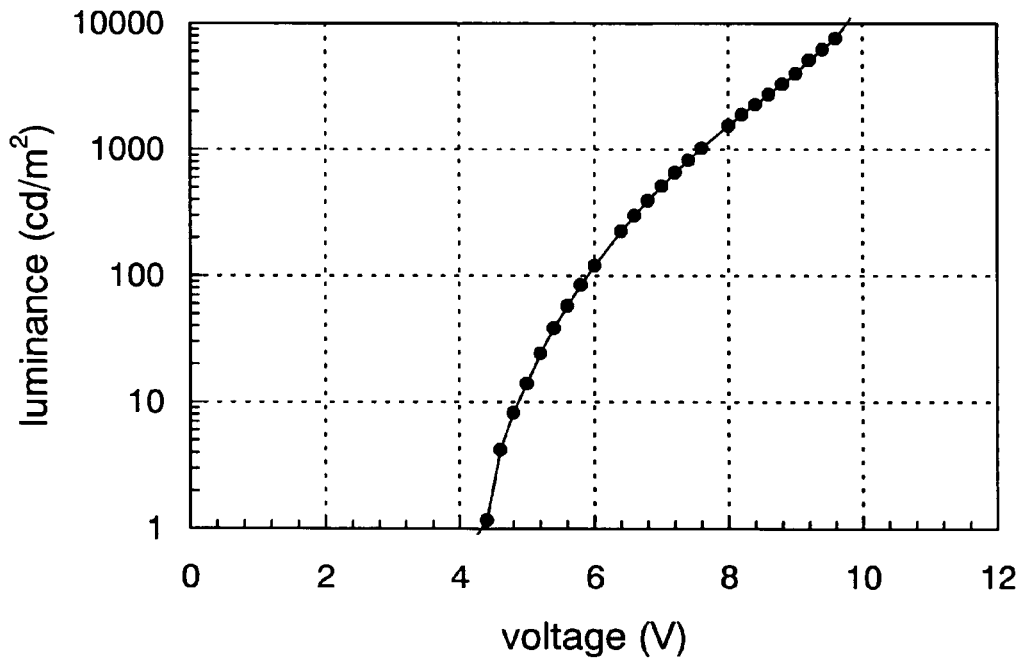
FIG. 14 is a graph showing voltage-luminance characteristics of a light emitting element of the present invention.
Figure 15:
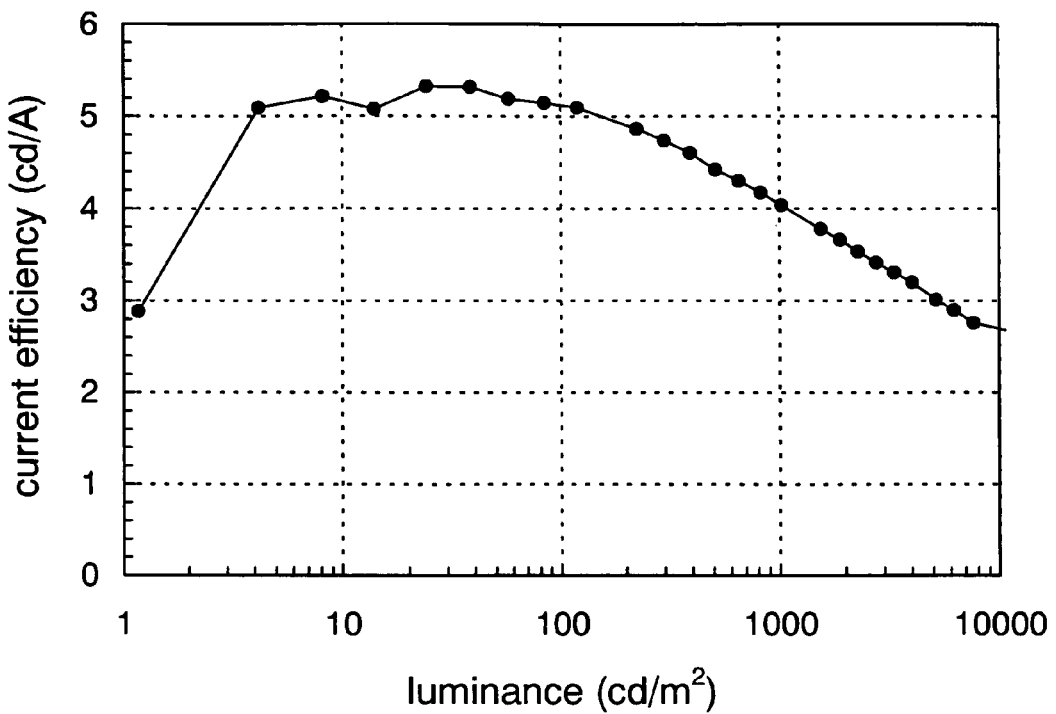
FIG. 15 is a graph showing a luminance-current efficiency characteristics of a light emitting element of the present invention.

FIGS. 13 to 15 respectively show a measurement result of current density-luminance characteristics, voltage-luminance characteristics, and luminance-current efficiency characteristics. In FIG. 13, the horizontal axis indicates a current density (mA/cm$^2$), and the vertical axis indicates a luminance (cd/m$^2$). In FIG. 14, the horizontal axis indicates a voltage (V), and the vertical axis indicates a luminance (cd/m$^2$). In FIG. 15, the horizontal axis indicates a luminance (cd/m$^2$), and the vertical axis indicates current efficiency (cd/A). In accordance with these results, it was determined that a current flows with the current density of 25.4 mA/cm$^2$ when a voltage of 7.6 V is applied, light is emitted with a luminance of 1020 cd/m$^2$ in the light emitting element of the present embodiment. The current efficiency at this time was 4.03 cd/A. Further, the chromaticity coordinates in CIE colorimetric system at this time were (x,y)=(0.68, 0.30) and it was determined that the light emitting element in the present embodiment exhibits red light with favorable color purity.

Figure 16:
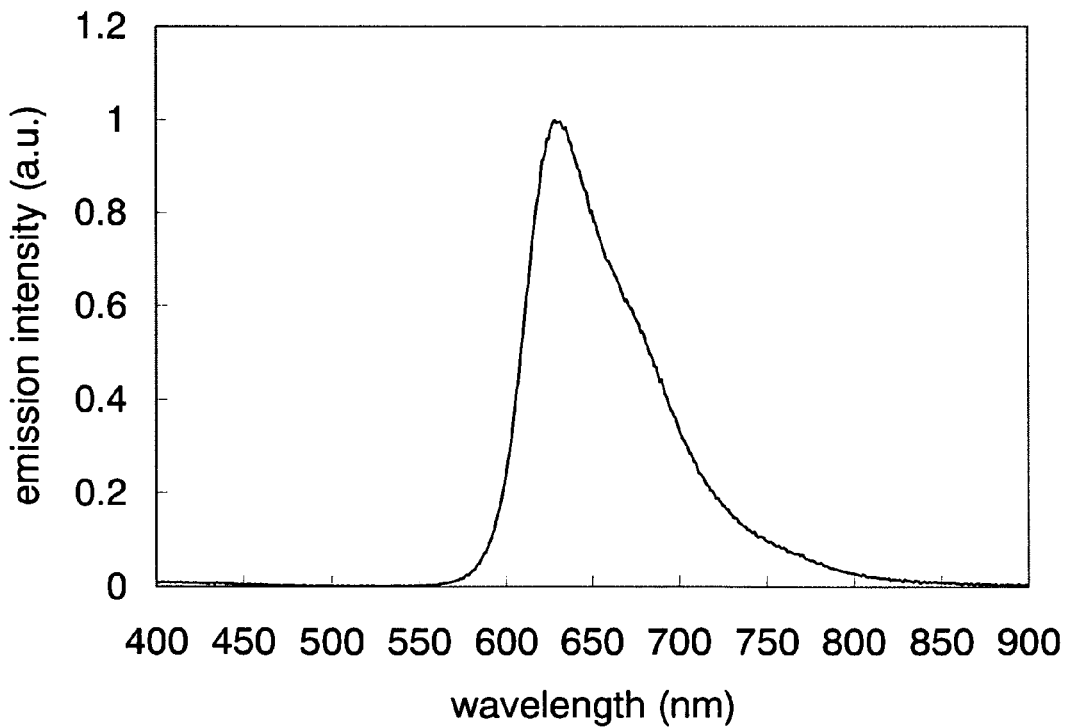
FIG. 16 is a graph showing current density-luminance characteristics of a light emitting element of the present invention.

FIG. 16 shows an emission spectrum in the case where a current flows with the current density of 25 mA/cm$^2$ to the light emitting element manufactured in the present embodiment. In FIG. 16, the horizontal axis indicates a wavelength (nm), and the vertical axis indicates emission intensity (arbitrary unit). In accordance with FIG. 16, it was determined that the light emitting element of the present embodiment has a peak of the emission spectrum at 629 nm and exhibits luminescence derived from Ir(CF$_3$dpq)$_2$(pic).

The invention claimed is:

1. An organometallic complex represented by a structural formula (12)

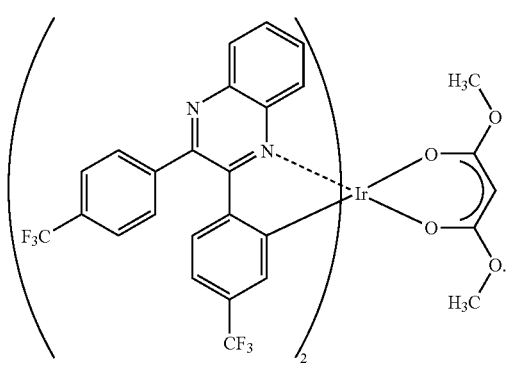

2. An organometallic complex represented by a structural formula (13)

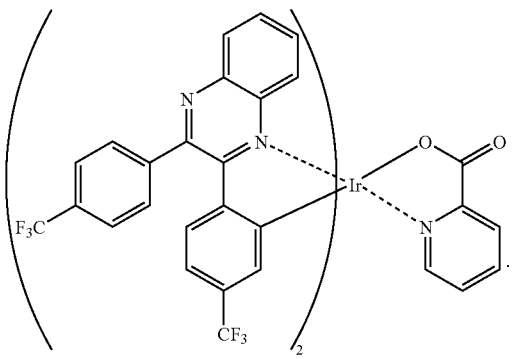

3. An organometallic complex represented by a structural formula (14)

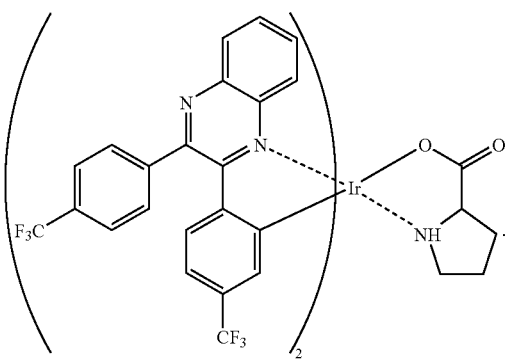

4. An organometallic complex represented by a structural formula (15)

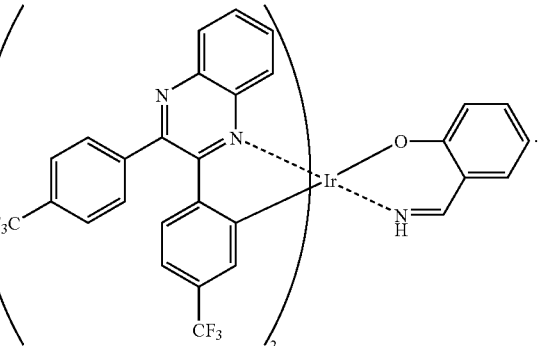

5. An organometallic complex represented by a structural formula (16)

(16)

6. An organometallic complex represented by a structural formula (17)

(17)

7. An organometallic complex represented by a structural formula (10)

(10)

8. A photoelectronics device including the organometallic complex according to claim 7.

9. A light emitting element comprising a layer including the organometallic complex according to claim 7 between a pair of electrodes.

10. A light emitting device, in which a plurality of the light emitting elements according to claim 9 are arranged.

11. An electronic equipment using the light emitting device according to claim 10 in a display portion.

12. A light emitting element using the organometallic complex according to claim 7 as a luminescent substance.

13. A light emitting element using the organometallic complex according to claim 7 as a sensitizer of a fluorescent compound.

14. A photoelectronics device including the organometallic complex according to claim 1.

15. A light emitting element comprising a layer including the organometallic complex according to claim 1 between a pair of electrodes.

16. A light emitting device, in which a plurality of the light emitting elements according to claim 15 are arranged.

17. An electronic equipment using the light emitting device according to claim 16 in a display portion.

18. A light emitting element using the organometallic complex according to claim 1 as a luminescent substance.

19. A light emitting element using the organometallic complex according to claim 1 as a sensitizer of a fluorescent compound.

20. A photoelectronics device including the organometallic complex according to claim 2.

21. A light emitting element comprising a layer including the organometallic complex according to claim 2 between a pair of electrodes.

22. A light emitting device, in which a plurality of the light emitting elements according to claim 21 are arranged.

23. An electronic equipment using the light emitting device according to claim 22 in a display portion.

24. A light emitting element using the organometallic complex according to claim 2 as a luminescent substance.

25. A light emitting element using the organometallic complex according to claim 2 as a sensitizer of a fluorescent compound.

26. A photoelectronics device including the organometallic complex according to claim 6.

27. A light emitting element comprising a layer including the organometallic complex according to claim 3 between a pair of electrodes.

28. A light emitting device, in which a plurality of the light emitting elements according to claim 27 are arranged.

29. An electronic equipment using the light emitting device according to claim 28 in a display portion.

30. A light emitting element using the organometallic complex according to claim 3 as a luminescent substance.

31. A light emitting element using the organometallic complex according to claim 3 as a sensitizer of a fluorescent compound.

32. A photoelectronics device including the organometallic complex according to claim 4.

33. A light emitting element comprising a layer including the organometallic complex according to claim 4 between a pair of electrodes.

34. A light emitting device, in which a plurality of the light emitting elements according to claim 33 are arranged.

35. An electronic equipment using the light emitting device according to claim 34 in a display portion.

36. A light emitting element using the organometallic complex according to claim 4 as a luminescent substance.

37. A light emitting element using the organometallic complex according to claim 4 as a sensitizer of a fluorescent compound.

38. A photoelectronics device including the organometallic complex according to claim 5.

39. A light emitting element comprising a layer including the organometallic complex according to claim 5 between a pair of electrodes.

40. A light emitting device, in which a plurality of the light emitting elements according to claim 39 are arranged.

41. An electronic equipment using the light emitting device according to claim 40 in a display portion.

42. A light emitting element using the organometallic complex according to claim 5 as a luminescent substance.

43. A light emitting element using the organometallic complex according to claim 5 as a sensitizer of a fluorescent compound.

44. A photoelectronics device including the organometallic complex according to claims 6.

45. A light emitting element comprising a layer including the organometallic complex according to claim 6 between a pair of electrodes.

46. A light emitting device, in which a plurality of the light emitting elements according to claim 45 are arranged.

47. An electronic equipment using the light emitting device according to claim 46 in a display portion.

48. A light emitting element using the organometallic complex according to claim 6 as a luminescent substance.

49. A light emitting element using the organometallic complex according to claim 6 as a sensitizer of a fluorescent compound.

* * * * *

UNITED STATES PATENT AND TRADEMARK OFFICE
CERTIFICATE OF CORRECTION

PATENT NO. : 7,771,844 B2  Page 1 of 1
APPLICATION NO. : 11/274327
DATED : August 10, 2010
INVENTOR(S) : Hideko Inoue et al.

It is certified that error appears in the above-identified patent and that said Letters Patent is hereby corrected as shown below:

At column 15, line 19, please change "alight" to --a light--;

At column 18, line 10, please change "alight" to --a light--;

At column 25, line 4, please change "n-throw" to --n-th row--;

At column 36, line 22, please change "ref lux" to --reflux--;

At column 42, line 39, please change "claim 6" to --claim 3--;

At column 43, line 14, please change "claims 6" to --claim 6--.

Signed and Sealed this

Twenty-third Day of November, 2010

David J. Kappos
*Director of the United States Patent and Trademark Office*